US011629356B2

(12) United States Patent
Xie et al.

(10) Patent No.: US 11,629,356 B2
(45) Date of Patent: Apr. 18, 2023

(54) REGULATING LIGNIN BIOSYNTHESIS AND SUGAR RELEASE IN PLANTS

(71) Applicant: UT-Battelle, LLC, Oak Ridge, TN (US)

(72) Inventors: Meng Xie, Oakridge, TN (US); Wellington Muchero, Oakridge, TN (US); Jin-Gui Chen, Oak Ridge, TN (US); Gerald A. Tuskan, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 16/890,157

(22) Filed: Jun. 2, 2020

(65) Prior Publication Data
US 2020/0377903 A1    Dec. 3, 2020

Related U.S. Application Data

(60) Provisional application No. 62/856,172, filed on Jun. 3, 2019.

(51) Int. Cl.
*C12N 15/82* (2006.01)
*C12N 15/90* (2006.01)
*C12N 9/22* (2006.01)

(52) U.S. Cl.
CPC .......... *C12N 15/8255* (2013.01); *C12N 9/22* (2013.01); *C12N 15/902* (2013.01); *C12N 2310/20* (2017.05)

(58) Field of Classification Search
None
See application file for complete search history.

(56) References Cited

PUBLICATIONS

Rubin, Structure and Evolution of the hAT Transposon Superfamily, Genetics Society of America, 2001 (Year: 2001).*
Knip, The SLEEPER genes: a transposase-derived angiosperm-specific gene family, BMC Plant Biology, 2012 (Year: 2012).*
Genbank Accession XM_011016059, Predicted: Populus euphratica zinc finger BED domain-containing RICESLEEPER 2-like (LOC105118170), transcript variant X2, mRNA, Jan. 6, 2015 (Year: 2015).*
Genbank Accession XP_011014360, Predicted: zinc finger BED domain-containing protein RICESLEEPER 2-like isoform X1 [Populus euphratica], Jan. 6, 2015 (Year: 2015).*
XM_024588163.1, Predicted: Populus trichocarpa zinc finger BED domain-containing protein RICESLEEPER 1 (LOC18106085), mRNA, GenBank, Apr. 9, 2018 (Year: 2018).*
XP_024443931.1 (Protein), zinc finger BED domain-containing protein RICESLEEPER 1 [Populus trichocarpa], GenBank, Apr. 9, 2018 (Year: 2018).*
Barros, J. et al., "The cell biology of lignification in higher plants", Annals of Botany, vol. 115, pp. 1053-1074 (2015).

Fraser, C.M. et al.,"The Phenylpropanoid Pathway in *Arabidopsis*", The *Arabidopsis* Book 9, pp. 1-19 (Dec. 8, 2011).
Goicoechea, M. et al., "EgMYB2, a new transcriptional activator from Eucalyptus xylem, regulates secondary cell wall formation and lignin biosynthesis", The Plant Journal, vol. 43, pp. 553-567 (2005).
Hinchee, M. et al., "Short-rotation woody crops for bioenergy and biofuels applications", In Vitro Cell. Dev. Biol., vol. 45, pp. 619-629 (2009).
Kim, W.C. et al., "Identification of direct targets of transcription factor MYB46 provides insights into the transcriptional regulation of secondary wall biosynthesis", Plant Mol. Biol., vol. 85, pp. 589-599 (2014).
McCarthy, R.L. et al., "The Poplar MYB Transcription Factors, PtrMYB3 and PtrMYB20, are Involved in the Regulation of Secondary Wall Biosynthesis", Plant Cell Physiol., 51(6): 1084-1090 (2010).
Ohashi-Ito, K. et L., "*Arabidopsis* Vascular-Related NAC-DOMAIN6 Directly Regulates the Genes That Govern Programmed Cell Death and Secondary Wall Formation during Xylem Differentiation", The Plant Cell, vol. 22, pp. 3461-3473 (Oct. 2010).
Patzlaff, A. et al., "Characterisation of a pine MYB that reguates lignification", The Plant Journal, vol. 36, pp. 743-754 (2003).
Ragauskas, A.J. et al., The Path Forward for Biofuels and Biomaterials, Science, vol. 311, pp. 484-489 (Jan. 27, 2006).
Tohge, T. et al.,"Shikimate and phenylalanine biosynthesis in the green lineage", Frontiers in Plant Science, 4(62): 1-13 (Mar. 27, 2013).
VanHolme, R. et al.,"Lignin Biosynthesis and Structure", Plant Physiology, vol. 153, pp. 895-905 (Jul. 2010).
Vogt, T., "Phenylpropanoid Biosynthesis", Molecular Plant, 3(1):2-20 (Jan. 2010).
Weng, J-K. et al.,"Emerging strategies of lignin engineering and degradation for cellulosic biofuel production", Current Opinion in Biotechnology, vol. 19, pp. 116-172 (2008).
Wilkins, O. et al., "Expansion and Diversification of the Populus R2R3-MYB Family of Transcription Factors", Plant Physiology, vol. 149, pp. 981-993 (Feb. 2009).
Yamaguchi, M. et al.,"Vascular-Related NAC-DOMAIN 7 directly regulates the expression of a broad range of genes for xylem vessel formation", The Plant Journal, vol. 65, pp. 579-590 (2011).
Zhong, R. et al., "The MYB46 Transcription Factor Is a Direct Target of SND1 and Regulates Secondary Wall Biosynthesis in *Arabidopsis*", The Plant Cell, vol. 19, pp. 2776-2792 (Sep. 2007).
Zhong, R et al., "The poplar PtrWNDs are transcriptional activators of secondary cell wall biosynthesis", Plant Signaling & Behavior, 5:4, pp. 469-472 (2010).

(Continued)

*Primary Examiner* — Weihua Fan
*Assistant Examiner* — Brian James Sullivan
(74) *Attorney, Agent, or Firm* — Scully, Scott, Murphy & Presser, P.C.

(57) ABSTRACT

This disclosure provides genetically modified plants, plant cells and plant tissues that show modified lignin content and/or sugar release as compared to a wild type control plant which was not genetically modified. In addition, the disclosure provides methods of regulating lignin content and sugar release in a plant. The disclosure also provides methods of producing bioproducts using the genetically modified plants of the instant disclosure.

9 Claims, 12 Drawing Sheets
(11 of 12 Drawing Sheet(s) Filed in Color)
Specification includes a Sequence Listing.

(56) References Cited

PUBLICATIONS

Zhong, R. et al., "The Poplar MYB Master Switches Bind to the SMRE Site and Activate the Secondary Wall Biosynthetic Program during Wood Formation", PLos One, 8 (7), e 69219, pp. 1-13 (Jul. 2013).

* cited by examiner

A

B

C

D

E

A

B

REGULATING LIGNIN BIOSYNTHESIS AND SUGAR RELEASE IN PLANTS

CROSS REFERENCE TO RELATED APPLICATION

This application claims the benefit of priority from U.S. Provisional Application No. 62/856,172, filed Jun. 3, 2019, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in the ASCII text file, named as 38353_3891_2_Seqlist_ST25.txt of 30 KB, created on May 18, 2020, and submitted to the United States Patent and Trademark Office via EFS-Web, is incorporated herein by reference.

BACKGROUND

Quantitative Evolution of the phenylpropanoid pathway has been proposed as one of the primary events leading to successful colonization of terrestrial environments by plants (Tohge T. et al. (2013). *Front. Plant Sci.* 4: 62). Specifically, lignin biosynthesis evolved from the phenylpropanoid pathway to overcome obstacles related to structural support and defense against biotic and abiotic stresses as plants moved from aquatic to terrestrial environments (Weng J.-K. et al. (2008). *Curr. Opin. Biotechnol.* 19: 166-172). Long-lived perennial plants, which cover approximately one-third of the Earth's terrestrial surface, are of special economic and ecological importance providing woody biomass as renewable feedstock for materials and energy while harboring substantial biodiversity and providing immeasurable environmental services (Achard F. (2009). *Vital Forest Graphics.* (Arendal, Norway: UNEP/GRID-Arendal); Hinchee M. et al. (2009). *Dev. Biol.* 45: 619-629; Ragauskas A. J. et al. (2006). *Science* 311: 484-489). Unlike herbaceous plants, woody plants exhibit extensive cell division and secondary cell wall thickening to generate biomass from secondary xylem tissue (Iqbal M. (1990). *The Vascular Cambium.* (Taunton, UK: Research Studies Press)).

Carbon flow into the phenylpropanoid pathway is vital for terrestrial plants as it provides precursors for secondary metabolites including monolignols (Barros J. et al., (2015). *Ann. Bot.* 115: 1053-1074). Besides monolignols, the phenylpropanoid pathway also provides precursors for various nonstructural, carbon-rich secondary metabolites, such as flavonoid, isoflavonoids and coumarins, which have important functions in plant defense against pathogens and predators (Fraser C. M., and Chapple C. (2011). *The Arabidopsis Book* 9: e0152.doi/10.1199/tab.0152; Vogt T. (2010). *Mol. Plant* 3: 2-20). The phenylpropanoid pathway begins at phenylalanine, an end-product of the shikimate pathway (Fraser C. M., and Chapple C. (2011), *The Arabidopsis Book* 9: e0152.doi/10.1199/tab.0152). After three reactions, carbon precursors from phenylalanine are transferred to 4-coumaroyl CoA, which serves as the precursor of all downstream phenylpropanoids, including lignin and nonstructural metabolites. Consequently, most lignin biosynthetic enzymes also play critical roles in the phenylpropanoid pathway, such as phenylalanine ammonia-lyase (PAL), cinnamate 4-hydroxylase (C4H), 4-coumarate:coa ligase (4CL), hydroxycinnamoyl-coenzyme a shikimate:quinate hydroxy-cinnamoyl-transferase (HCT), pcoumaroyl shikimate 3' hydroxylase (C3H), caffeoyl coa 3-omethyltransferase (CCoAOMT), cinnamoyl-coenzyme a reductase (CCR), cinnamyl alcohol dehydrogenase (CAD), ferulate 5-hydroxylase (F5H), and laccase (Vanholme R. et al. (2010). *Plant Physiol.* 153: 895-905; Vogt T. (2010). *Mol. Plant* 3: 2-20).

The transcription factor MYB Domain Protein 46 (MYB46) is one of the master regulators of the phenylpropanoid pathway and lignin biosynthesis in plant species. Genetic and biochemical studies in *Arabidopsis thaliana* have demonstrated that MYB46 directly targets and activates the expression of multiple lignin biosynthetic genes, including PAL1, C4H, 4CL, HCT, C3H1, F5H1, CCR, CAD6, and CCoAOMT1 (Kim W.-C. et al. (2014). *Plant Mol. Biol.* 85: 589-599). In addition to lignin biosynthetic genes, MYB46 also activates the expression of MYB58 and MYB63, two master regulators of lignin biosynthesis (Kim W.-C. et al. (2014). *Plant Mol. Biol.* 85: 589-599). Consistent with transcriptional data, transgenic *Arabidopsis* plants overexpressing MYB46 displayed ectopic lignin deposition in stem cells (Kim W.-C. et al. (2014). *Plant Mol. Biol.* 85: 589-599). Besides *Arabidopsis*, pine (*Pinus taeda*) and cider gum (*Eucalyptus gunnii*) MYB46 homologs were found to be functional in the regulation of the phenylpropanoid pathway and lignin biosynthesis (Goicoechea M. et al. (2005). *Plant J.* 43: 553-567; Patzlaff A. et al. (2003). *Plant J.* 36: 743-754). Phylogenetic analyses identified four close homologs of MYB46 in *Populus trichocarpa*: PtrMYB002, PtrMYB003, PtrMYB020, and PtrMYB021 (McCarthy R. L. et al. (2010) *Plant Cell Physiol.* 51: 1084-1090; Wilkins O. et al.(2009). *Plant Physiol.* 149: 981-993). All these four genes are functional because the heterologous expression of each gene in *Arabidopsis* could induce ectopic lignin deposition, which was observed in plants overexpres sing the *Arabidopsis* MYB46 (McCarthy et al., (2010), *Plant Cell Physiol.* 51: 1084-1090; Zhong R. et al. (2013). *PLoS One* 8: e69219). Transient expression assays in protoplasts demonstrated that the four *Populus* MYB46 genes were able to activate promoters of *Populus* lignin biosynthetic genes, such as 4CL1, CCoAOMT1, and caffeic acid o-methyltransferase 2 (COMT2) (McCarthy R. L. et al. (2010) *Plant Cell Physiol.* 51: 1084-1090; Zhong R. et al. (2013). *PLoS One* 8: e69219). Moreover, in transgenic *Populus* plants overexpressing PtrMYB003 or PtrMYB021, lignin was ectopically deposited in cell walls of stem cells (Zhong R. et al. (2013). *PLoS One* 8: e69219).

MYB46 is one master regulator of secondary cell wall biosynthesis and lignin biosynthesis and functions as transcriptional regulator of phenylpropanoid, tyrosine, tryptophan and flavonoid pathways. The identification of key genetic regulators of MYB46 is one of the critical steps for the production of plant-based flavonoids with medicinal or therapeutic applications, the production of biofuel, and the engineering of pathogen resistant strains to benefit consumer or farmer. Only genes positively regulate the expression level of MYB46 have been identified. However, genes negatively regulate MYB46 expression remain unidentified, which limits the flexible modulation of MYB46 expression.

In addition to lignin biosynthesis, *Arabidopsis* and *Populus* MYB46s also regulate the biosynthesis of other major components of the secondary cell wall including cellulose and xylan. The expression of cellulose synthases (CesAs) and xylan synthetic genes (IRREGULAR XYLEM, IRXs) could be directly activated by both *Arabidopsis* and *Populus* MYB46s (Kim et al., 2014; Kim et al., 2013b; McCarthy et al., 2010; Zhong et al., 2013). Because of the ability to activate the biosynthesis of all three major components of the secondary cell wall, MYB46 has been defined as one master regulator of secondary cell wall biosynthesis and wood formation. On the other hand, MYB46 is also under transcriptional regulation during secondary cell wall formation. NAC transcription factors, including SECONDARY WALL-ASSOCIATED NAC DOMAIN PROTEIN 1 (SND1), VASCULAR-RELATED NAC DOMAIN 6 (VND6), and VND7, were found to directly activate MYB46 expression in *Arabidopsis* (Ohashi-Ito K. et al. (2010), *Plant Cell* 22: 3461-3473; Yamaguchi M. et al. (2011), *Plant J.* 66: 579-590; Zhong R. et al. (2007), *Plant Cell* 19: 2776-2792). In *Populus*, the activation of MYB46 expression by a set of SND1 homologs (PtrWNDs) has been confirmed (Zhong R. et al. (2010), *Behav.* 5: 469-472). However, since perennial woody species clearly possess unique attributes during cell wall biosynthesis, little is known about their regulatory repertoire outside of those inferred from model systems.

BRIEF SUMMARY OF THE DISCLOSURE

In one aspect, this disclosure provides a genetically modified plant, plant cell or plant tissue, the genetic modification comprising at least one of: (a) expressing an exogenous nucleic acid comprising a PtrhAT gene or a homolog thereof, in the plant, plant cell or plant tissue; (b) introducing a mutation to an endogenous PtrhAT gene or a homolog thereof; (c) inactivating the endogenous PtrhAT gene or a homolog thereof.

In some embodiments, the exogenous nucleic acid comprises a sequence with at least 90% sequence homology to SEQ ID NO: 1. In some embodiments, the exogenous nucleic acid encodes a protein with at least 90% sequence homology to SEQ ID NO: 2. In some embodiments, the exogenous nucleic acid is stably integrated into the plant genome.

In some embodiments, the mutation to the endogenous PtrhAT gene results in loss of DNA binding activity of the PtrhAT protein, or the resulting mutant PtrhAT gene has at least 90% sequence homology to SEQ ID NO: 1 or the mutant PtrhAT protein has at least 90% sequence homology to SEQ ID NO: 2.

In some embodiments, the mutation is introduced by genome editing, which is achieved by a method selected from the group consisting of a CRISPR/Cas system, a Cre/Lox system, a TALEN system, a ZFNs system and homologous recombination.

In some embodiments, the CRISPR/Cas system comprises introducing into the plant a first nucleic acid encoding a Cas9 or Cas12 nuclease, a second nucleic acid comprising a guide RNA (gRNA), and a third nucleic acid comprising a homologous repair template of a PtrhAT gene comprising at least one mutation in the PtrhAT gene sequence that results in loss of DNA binding activity, resulting in an increased lignin content and/or a reduced sugar release in the plant.

In some embodiments, the inactivation of the PtrhAT gene is achieved by introducing a nucleic acid inhibitor of the PtrhAT gene to the plant.

In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the PtrhAT gene is achieved by genome editing, which is achieved by a method selected from the group consisting of a CRISPR/Cas system, a Cre/Lox system, a TALEN system, a ZFNs system and homologous recombination.

In some embodiments, the CRISPR-mediated genome editing comprises introducing into the plant a first nucleic acid encoding a Cas9 nuclease, a second nucleic acid comprising a guide RNA (gRNA), wherein the gRNA is specific to the PtrhAT gene.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea,* and *Zoysia*.

Another aspect of the disclosure is directed to a method comprising genetically modifying a plant, plant cell or plant tissue, wherein the genetic modifying comprises at least one of: (a) expressing an exogenous nucleic acid encoding a PtrhAT gene or a homolog thereof, in the plant, plant cell or plant tissue; (b) introducing a mutation to an endogenous PtrhAT gene or a homolog thereof, in the plant, plant cell or plant tissue; or (c) inactivating the endogenous PtrhAT gene or a homolog thereof, in the plant, plant cell or plant tissue.

In some embodiments, the exogenous nucleic acid comprises a sequence with at least 90% sequence homology to SEQ ID NO: 1. In some embodiments, the exogenous nucleic acid encodes a protein with at least 90% sequence homology to SEQ ID NO: 2. In some embodiments, the exogenous nucleic acid is stably integrated into the plant genome.

In some embodiments, the introduced mutation results in loss of DNA binding activity of the mutant PtrhAT gene and has at least 90% sequence homology to SEQ ID NO: 1 or the mutant PtrhAT protein and has at least 90% sequence homology to SEQ ID NO: 2.

In some embodiments, the mutation is introduced by genome editing, which is achieved by a method selected from the group consisting of a CRISPR/Cas system, a Cre/Lox system, a TALEN system, a ZFNs system and homologous recombination.

In some embodiments, the CRISPR/Cas system comprises introducing into the plant a first nucleic acid encoding a Cas9 or Cas12 nuclease, a second nucleic acid comprising a guide RNA (gRNA), and a third nucleic acid comprising a homologous repair template of a PtrhAT gene comprising at least one mutation in the PtrhAT gene sequence that results in loss of DNA binding activity.

In some embodiments, the inactivation of the PtrhAT gene is achieved by introducing a nucleic acid inhibitor of the PtrhAT gene to the plant.

In some embodiments, the nucleic acid inhibitor is selected from the group consisting of an antisense RNA, a small interfering RNA, an RNAi, a microRNA, an artificial microRNA, and a ribozyme. In some embodiments, the inactivation of the PtrhAT gene is achieved by genome editing, which is achieved by a method selected from the group consisting of a CRISPR/Cas system, a Cre/Lox system, a TALEN system, a ZFNs system and homologous recombination.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the PtrhAT gene.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

Another aspect of the disclosure is directed to a method for producing a bioproduct, comprising subjecting the genetically modified plant, plant cell or plant tissue of the disclosure to a bioproduct conversion process. In some embodiments, the bioproduct is selected from the group consisting of a bioenergy product, a biomaterial, a biopharmaceutical and a biocosmetics. In some embodiments, the bioenergy product is ethanol and the bioproduct conversion process is an ethanol fermentation process. In some embodiments, the bioproduct is selected from the group consisting of ethanol, biodiesel, biogas, bioplastics, biofoams, biorubber, biocomposites, and biofibres.

Another aspect of the disclosure is directed to a method for production of pulp or paper, comprising producing pulp or paper from the genetically modified plant of the instant disclosure.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Definitions

Figure 1A:
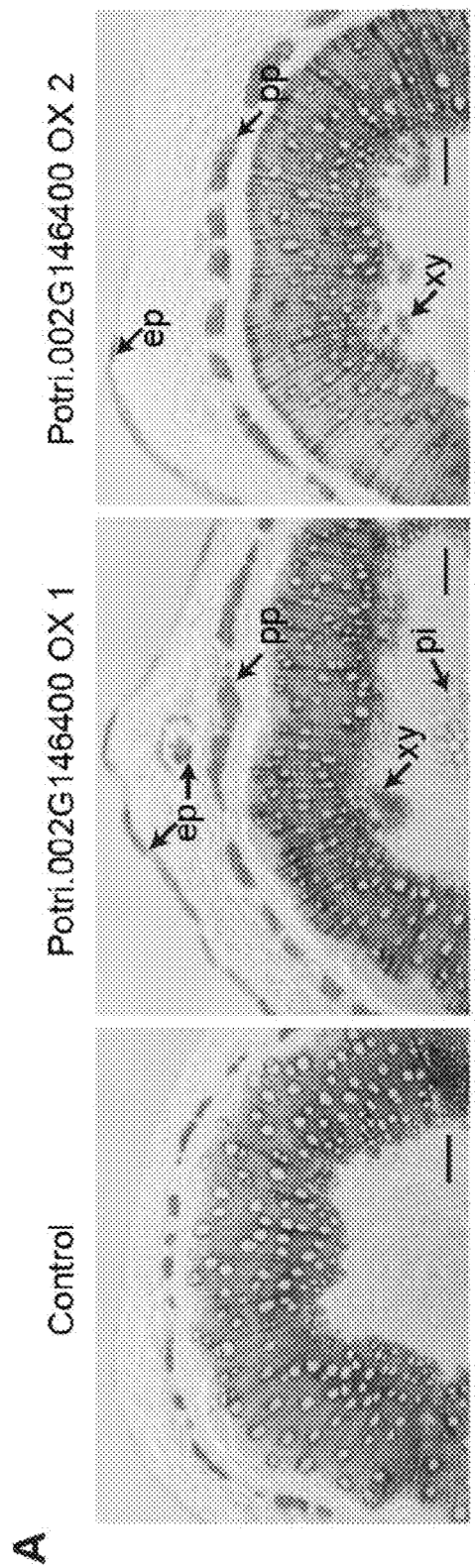
FIGS. 1A-1B. Potri.002G146400 affects the phenylpropanoid pathway and lignin biosynthesis. (A) Phloroglucinol-HCl staining of stems from transgenic *Populus* plants overexpressing Potri.002G146400. Ectopic lignin depositions in different tissues are illustrated by black arrows. ep, epidermis; pp, phloem fibers; xy, secondary xylem; pi, pith cells. Scale bar: 200 µm. (B) Changes of phenylpropanoid pathway metabolites in two independent Potri.002G146400 overexpression plants. Up-regulated metabolites in both transgenic lines are in red.

Unless defined otherwise, all technical and scientific terms used herein have the same meaning as commonly understood by one of ordinary skill in the art to which this invention belongs.

As used herein, the term "about" refers to an approximately +/−10% variation from a given value.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "DNA," as used herein, refers to a nucleic acid molecule of one or more nucleotides in length, wherein the nucleotide(s) are nucleotides. By "nucleotide" it is meant a naturally-occurring nucleotide, as well as modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

The term "homolog" means a gene related to a second gene by descent from a common ancestral DNA sequence, therefore, the corresponding polynucleotide/polypeptide has a certain degree of homology, i.e., sequence identity (at least 40%, at least 60%, at least 65%, particularly preferred at least 66%, 68%, 70%, 75%, 80%, 86%, 88%, 90%, 91%, 92%, 93%, 94%, 95%, 96%, 97%, 98% or 99% sequence identity). A "homolog" furthermore means that the function is equivalent to the function of the original gene. Homologs of a given gene and homologous positions in the gene can be determined by sequence alignment programs, e.g., including but not limited to, NCBI BLAST, ClustalW, DIAMOND, CS-BLAST, and MAFFT.

As used herein, the term "nucleic acid" has its general meaning in the art and refers to a coding or non coding nucleic acid sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e., nuclear or mitochondrial).

A "nucleic acid inhibitor" is a nucleic acid that can reduce or prevent expression or activity of a target gene. For example, an inhibitor of expression of a gene can reduce or eliminate transcription and/or translation of the gene product, thus reducing the gene protein expression.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

"Sugar release" includes high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant or genetic modification. "Low" sugar release (i.e., high recalcitrance) means that sugar can be extracted less easily, or less sugar can be extracted, from a plant, under conditions that would result in more sugar release in a plant without the particular allelic variant or genetic modification. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Altered (increased or decreased) sugar release may be due to altered S/G ratio in a plant. Altered S/G ratios in a plant (e.g., *Populus* species) include, for example, alterations from about 50% syringyl ("S"):50% guaiacyl ("G") units to about 100% syringyl units, or about 100% guaiacyl units. The terms "units" and "subunits" are used interchangeably herein. Specific S/G ratios include, for example, greater than 2:1, e.g., 2.1:1, 2.2:1, 2.5:1, 2.8:1, 3.0:1, 3.5:1, 4:1, etc; or less than 2:1, e.g., 0.5:1, 0.8:1, 1:1, 1.2:1, 1.5:1, 1.8:1, or 2:1.3, 2:1.5, 2:1.7, 2:1.9, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant. In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

G units have greater capacity for cross-linking between monomers relative to S units. Thus, increasing the ratio of S/G subunits to greater than 2:1 increases S subunits and decreases G subunits in lignin and thus decreases cross-linking between subunits incorporated into lignin. This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in *Populus* at values above 2.0. The exact way this occurs is not known though it is speculated that lignin remains intact during saccharification under high temperature and/or pressure. Nevertheless, biomass with an S/G ratio above 2.0 releases more sugar.

Sugar release can be measured, for example, by saccharification analysis. In one example of saccharification analysis, sugars are extracted with alpha-amylase and β-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/ release, such as by addition of glucose oxidase/peroxidase for measuring glucose content, and/or xylose dehydrogenase to measure xylose content.

High or low sugar release can be an increase or decrease in sugar release or sugar recovery of 2%, 5%, 8%, 10%, 15%, 20%, 25%, 30%, 40%, 50%, 60%, 70%, 80%, 90%, or 100% in a plant with a particular modulation of the PtrhAT gene, relative to sugar release or sugar recovery from a plant that does not have the modulation of the PtrhAT gene. In one example, "low" glucose release is glucose release of less than 0.1, 0.15, 0.2, or 0.25 g glucose per g biomass. "High" glucose release is glucose release of 0.3, 0.35, 0.4, or 0.45 g glucose per g biomass or more. "Low" glucose/xylose release is combined release of glucose and xylose of less than 0.2, 0.25, 0.3, 0.35, or 0.4 g combined glucose/xylose per g biomass. "High" glucose/xylose release is combined release of glucose and xylose above 0.4, 0.45, 0.5, 0.55, or 0.6 g combined glucose/xylose per g biomass.

Lignin forms strong bonds with sugars and interferes with access to these carbohydrates, making it difficult to extract the plant's sugars contained in cellulose and hemicellulose. Differences in lignin content alter the sugar release properties of a plant in the extraction process. Lower lignin levels in a plant are associated with higher levels of sugar release, while higher lignin levels are associated with lower levels of sugar release. Thus, sugar release and lignin content can show an inverse correlation. In addition, the higher interactions of cell wall components (including lignins) also determine the amount of sugar that can be released.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

The term "variant," as used herein, refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

General Description

Genetically-Modified Plants, Plant Tissues or Plant Cells

Disclosed herein is a genetically-modified plant, plant tissue or plant cell that has modified lignin content and sugar release as compared to a wild type control plant. In some embodiments, the genetically modified plant has increased lignin content as compared to a wild type control plant. In some embodiments, the genetically modified plant has decreased lignin content as compared to a wild type control plant. In some embodiments, the genetically modified plant has increased sugar release as compared to a wild type control plant. In some embodiments, the genetically modified plant has decreased sugar release as compared to a wild type control plant. All the embodiments described herein for genetically modified plants are applicable to genetically modified plant cells and genetically modified plant tissues as well.

In some embodiments, the genetically-modified plant, plant tissue or plant cell expresses an exogenous nucleic acid encoding a PtrhAT gene, or a homolog thereof, in the plant, plant cell or plant tissue, resulting in decreased lignin content and increased sugar release in the plant, plant tissue or plant cell. In some embodiments, the PtrhAT gene comprises a sequence as shown in SEQ ID NO: 1, or a variant or homolog thereof. In some embodiments, the PtrhAT gene encodes a protein shown in SEQ ID NO: 2, or a variant or homolog thereof.

In some embodiments, the exogenous nucleic acid comprises a sequence with at least 90%, at least 91%, at least 92%, at least 93%, at least 94%, at least 95%, at least 96%, at least 97%, at least 98%, at least 99% sequence identity to SEQ ID NO: 1. In some embodiments, the exogenous nucleic acid encodes a protein with at least 90%, at least 91%, at least 92%, at least 93%, at least 94%, at least 95%, at least 96%, at least 97%, at least 98%, at least 99% sequence identity to SEQ ID NO: 2.

In some embodiments, the genetically-modified plant, plant tissue or plant cell comprises a mutation to an endogenous PtrhAT gene, or a homolog thereof.

In some embodiments, the mutation is introduced by genome editing, which is achieved by a method selected from the group consisting of CRISPR/Cas system, Cre/Lox system, TALEN system, ZFNs system and homologous recombination. In some embodiments, the CRISPR/Cas system comprises introducing into the plant a first nucleic acid encoding a Cas9 or Cas12 nuclease, a second nucleic acid comprising a guide RNA (gRNA), and a third nucleic acid comprising a homologous repair template of a PtrhAT gene comprising at least one mutation in the PtrhAT gene sequence that results in loss of DNA binding activity, resulting in increased lignin content and decreased sugar release in the plant as compared to a control wild type plant.

In some embodiments, the mutation to the endogenous PtrhAT gene results in loss of DNA binding activity of the PtrhAT protein. In some embodiments, the mutant PtrhAT gene has at least 90%, at least 91%, at least 92%, at least 93%, at least 94%, at least 95%, at least 96%, at least 97%, at least 98%, at least 99% sequence identity to SEQ ID NO: 1. In some embodiments, the mutant PtrhAT protein has at least 90%, at least 91%, at least 92%, at least 93%, at least 94%, at least 95%, at least 96%, at least 97%, at least 98%, at least 99% sequence identity to SEQ ID NO: 2.

In some embodiments, the genetically-modified plant, plant tissue or plant cell comprises a genetic modification that results in inactivation of the endogenous PtrhAT gene, or a variant or homolog thereof. In some embodiments, inactivation of the endogenous PtrhAT gene results in increased lignin content and/or decreased sugar release in the plant as compared to a wild type control plant.

In some embodiments, the inactivation of the PtrhAT gene is achieved by introducing a nucleic acid inhibitor of the PtrhAT gene to the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the PtrhAT gene is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the PtrhAT gene.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*. In a specific embodiment, the plant is rice *Oryza sativa* or *Oryza glaberrima*.

A plant or plant cell used in the instant disclosure may contain a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, genetically modified (transgenic) plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

Methods of Modulating Sugar Release and Lignin Content in a Plant

This disclosure further provides methods for regulating sugar release and lignin content of a plant.

In some embodiments, the methods of the instant disclosure comprise expressing an exogenous nucleic acid encoding a PtrhAT gene, or a homolog thereof, in a plant, plant cell or plant tissue, resulting in decreased lignin content and/or increased sugar release in the plant, plant tissue or plant cell as compared to a wild type control plant. In some embodiments, the PtrhAT gene comprises a sequence as shown in SEQ ID NO: 1, or a variant or homolog thereof. In some embodiments, the PtrhAT gene encodes a protein shown in SEQ ID NO: 2, or a variant or homolog thereof.

In some embodiments, the exogenous nucleic acid comprises a sequence with at least 90%, at least 91%, at least 92%, at least 93%, at least 94%, at least 95%, at least 96%, at least 97%, at least 98%, at least 99% sequence identity to SEQ ID NO: 1. In some embodiments, the exogenous nucleic acid encodes a protein with at least 90%, at least 91%, at least 92%, at least 93%, at least 94%, at least 95%, at least 96%, at least 97%, at least 98%, at least 99% sequence identity to SEQ ID NO: 2.

In some embodiments, the method comprises introducing a mutation to an endogenous PtrhAT gene, or a homolog thereof in a plant, plant tissue or plant cell, resulting in increased lignin content and decreased sugar release in the plant, plant tissue or plant cell as compared to a wild type control plant.

In some embodiments, the mutation is introduced by genome editing, which is achieved by a method selected from the group consisting of CRISPR/Cas system, Cre/Lox system, TALEN system, ZFNs system and homologous recombination. In some embodiments, the CRISPR/Cas system comprises introducing into the plant a first nucleic acid encoding a Cas9 or Cas12 nuclease, a second nucleic acid comprising a guide RNA (gRNA), and a third nucleic acid comprising a homologous repair template of a PtrhAT gene comprising at least one mutation in the PtrhAT gene sequence that results in loss of DNA binding activity, resulting in increased lignin content in the plant compared to a control wild type plant.

In some embodiments, the mutation to the endogenous PtrhAT gene results in loss of DNA binding activity of the PtrhAT protein. In some embodiments, the mutant PtrhAT gene has at least 90%, at least 91%, at least 92%, at least 93%, at least 94%, at least 95%, at least 96%, at least 97%, at least 98%, at least 99% sequence identity to SEQ ID NO: 1. In some embodiments, the mutant PtrhAT protein has at least 90%, at least 91%, at least 92%, at least 93%, at least 94%, at least 95%, at least 96%, at least 97%, at least 98%, at least 99% sequence identity to SEQ ID NO: 2.

In some embodiments, the method comprises inactivating endogenous PtrhAT gene, or a variant or homolog thereof, in a plant, plant tissue or plant cell, resulting in increased lignin content and decreased sugar release in the plant, plant tissue or plant cell as compared to a wild type control plant.

In some embodiments, the inactivation of the PtrhAT gene is achieved by introducing a nucleic acid inhibitor of the PtrhAT gene to the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the PtrhAT gene is achieved by genome editing, which is achieved by a method selected from the group consisting of CRISPR/Cas system, Cre/Lox system, TALEN system, ZFNs system and homologous recombination.

In one embodiment, gene inactivation is achieved by a CRISPR/Cas system. CRISPR-Cas and similar gene targeting systems are well known in the art with reagents and protocols readily available (Mali, P. et al., 2013. *Science,* 339(6121), 823-826; Hsu, P. D. et al., 2014. *Cell,* 157.6: 1262-1278; Jiang et al., 2013. *Nature Biotechnology,* 31, 233-239). Exemplary genome editing protocols are described in Jennifer Doudna, and Prashant Mali, 2016. *"CRISPR-Cas: A Laboratory Manual"* (CSHL Press, ISBN: 978-1-621821-30-4) and Ran, F. Ann, et al. 2013. *Nature Protocols,* 8 (11): 2281-2308.

A CRISPR endonuclease comprises two components: (1) an RNA-dependent nuclease, typically microbial Cas9; and (2) a short "guide RNA" (gRNA or sgRNA) comprising a −20 nucleotide targeting sequence that directs the nuclease to a location of interest in the genome. When co-expressed with an artificial sgRNA targeting a cellular gene, the Cas9 endonuclease generates double-stranded breaks of DNA at the targeted locus. In addition, when CRISPR endonuclease is supplemented with a stretch of DNA template homologous to the break region, the break is repaired using the supplied homologous DNA template via the process of homologous recombination (HR). CRISPR-mediated HR makes it possible to specifically edit the target DNA sequence and/or alter gene expression.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the PtrhAT gene.

By manipulating the PtrhAT gene, a PtrhAT homolog, or a transcription factor that is regulated by PtrhAT, the amount and/or rate of S subunit to G subunit biosynthesis, or the incorporation of S to G subunits into the lignin structure, can be altered. Alteration in the S/G subunit ratio alters the lignin composition of the plant cell wall.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*. In a specific embodiment, the plant is rice *Oryza sativa* or *Oryza glaberrima.*

Inhibitors and Expression Vectors for Modulating the Activity of Genes

Further disclosed herein are nucleic acid inhibitors of expression of endogenous PtrhAT, or a homolog or allelic variants thereof, to provide increased lignin content, high sugar release, and/or altered S/G ratio. Specific nucleic acid inhibitors include antisense RNA, small interfering RNA, RNAi, microRNA, artificial microRNA, and ribozymes.

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., 2000. *Plant Cell Rep*. V19:304-310; Chang and Yang, 1996. *Bot. Bull. Acad. Sin*., V37:35-40 and Han et al., Biotechnology in Agriculture and Forestry, V44:291 (ed. by Y. P. S. Bajaj), Springer-Vernag, (1999).

Nucleic Acid Inhibitors

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit the expression of PtrhAT, a PtrhAT homolog and/or a transcription factor that is regulated by PtrhAT in plants.

Suitable nucleic acid inhibitors, i.e., nucleic acids capable of inhibiting the expression of a target gene, include full-length nucleic acids of allelic variants of PtrhAT, a PtrhAT homolog and/or a PtrhAT allelic variant, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators

This disclosure provides an exogenous nucleic acid vector that comprises a nucleotide sequence that is transcribed into expression or overexpression of PtrhAT gene, or homolog thereof, that is functional in a plant.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab IR promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis* SUC2 sucrose-H+ symporter promoter (Truernit et al., *Planta,* 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate:CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At5g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell,* 3(10):1051-1061 (1991)), the Commelina yellow mottle virus (CoYMV) promoter (Medberry et al., *Plant Cell,* 4(2):185-192 (1992)) and the rice tungro baciliform virus (RTBV) promoter (Dai et al., *Proc. Natl. Acad. Sci. USA,* 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In one aspect, a plant cell comprising a PtrhAT nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of PtrhAT and/or PtrhAT allelic variant. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered lignin content, sugar release and cell wall structure.

Methods of Use of Genetically Modified (Transgenic) Plants

Disclosed herein are methods to increase glucose and/or xylose release in a plant or plant cell, or to alter lignin content, by expressing the disclosed inhibitors in plants and plant cells.

Further disclosed herein are improved methods of producing biofuel from cellulosic biomass, by using plants with a mutant PtrhAT, or homolog thereof, that lacks DNA binding ability in biofuel production processes. In some embodiments, the instant disclosure is directed to methods of producing biofuel from cellulosic biomass, by using plants wherein expression of endogenous PtrhAT, or homolog thereof, is inhibited. Methods of pretreatment and saccharification of biomass to fermentable sugars, followed by fermentation of the sugars to ethanol, are known in the art.

Articles of Manufacture

The materials and methods described herein are useful for modifying biomass characteristics, such as characteristics of biomass renewable energy source plants. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide altered lignin content in one or more tissues of plants grown from such seeds.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1

Materials and Methods

*Populus* Linkage Disequilibrium-Based Association Mapping

A genome-wide association mapping was performed using the *P. trichocarpa* mapping population that was genotyped using the *Populus* 34K Illumina Bead Array (Geraldes A., et al. (2013). *Mol. Ecol. Resour.* 13: 306-323) and phenotyped for cell wall chemistry as described previously (Muchero W., et al. (2015). *BMC Genomics* 16: 24). Lignin content was measured in increment cores collected from 683 mature trees in their native environment and 382 4-year-old trees grown in a field site at Clatskanie, Oreg. (46°6'11"N, 123°12'13"W) (Iqbal M. (1990). *The Vascular Cambium*. (Taunton, UK: Research Studies Press)). Genotype-phenotype associations were evaluated for 2,352 single nucleotide polymorphisms (SNPs) on chromosome II using the mixed linear model analysis with kinship and population structure as covariates (Yu J. et al. (2006). *Nat. Genet.* 38: 203-208). The analyses were carried out in TASSEL software (Maizegenetics website). Correction for multiple testing was performed using the False Discovery Rate (FDR) method (Benjamini Y., and Hochberg Y. (1995). *J. R. Stat. Soc. B* 57: 289-300).

PtrEPSP-TF Cloning and Generation of Transgenic *Populus*

Full-length Potri.002G146400 containing the HTH motif was cloned from a *P. deltoides* cDNA library via PCR using primers for sequences from Potri.002G146400: forward primer 5'-CACCCCCGGGAAAGCCATGGCT-CAAGTGA-3' (SEQ ID NO: 11) and reverse primer 5'-ACGCGTTTTGAGTGCAACTCAATGCTT-3' (SEQ ID NO: 12). For the PtrEPSP-TF RNAi lines, a 207-bp fragment was cloned using forward primer 5'-CACCCCCGGG-GAGGTTCTTGAGAGGTACAC-3' (SEQ ID NO: 13) and reverse primer 5'-TCTAGATTCA-CATATGACCAGTCTCCA-3' (SEQ ID NO: 14). For PtWND1B overexpression lines, the full-length coding region of PtWND1B (gene model: Potri.001G448400; 1235 bp) was amplified using the forward primer 5'-CACCCCCGGGATGCCTGAGGATATGATGAA-3' (SEQ ID NO: 15) and reverse primer 5'-ACGCGTTTGT-TATACCGATAAGTGGCAT-3' (SEQ ID NO: 16). The integrity of fragments was verified by DNA sequencing (ACGT, Inc.) after cloning into the Gateway® entry vector, pENTR/D-TOPO (Life Technologies). For PtrEPSP-TF overexpression and RNAi lines, the fragment was transferred to a binary Gateway® destination plasmid, pAGW560 (GenBank accession TBD), for overexpression and pAGW1176 (GenBank accession TBD) for knockdown using LR Clonase II recombination (Life Technologies). The resulting overexpression and knockdown cassettes comprised the *Arabidopsis* UBIQUITIN3 promoter, the PtrEPSP-TF coding or target sequence, and the nopaline synthase terminator. For PtWND1B overexpression lines, the gene fragment was subcloned into a binary vector under the control of vasculature-specific 4-coumurate CoA-ligase (4CL) promoter. The binary transformation vector was then transformed into *A. tumefaciens* strain EHA105 via electroporation. *P. deltoides* genotype WV94 was transformed using a modified *Agrobacterium*-based method (Mingozzi M. et al. (2009). *Tree Physiol.* 29: 333-343; Tsai C. J. et al. (1994) *Plant Cell Rep.* 14: 94-97). Shoots regenerated from isolated calli were tested using PCR to verify the presence of the transformed construct. Empty vector transformed plants were used as controls. Plants were propagated in a greenhouse maintained at 25° C. at 16 h day length.

Metabolite Profiling

Freeze-dried bark peels were ground with a micro-Wiley mill and ~50 mg DW was subsequently twice extracted with 2.5 mL 80% ethanol overnight and then combined prior to drying a 0.5 ml aliquot in a nitrogen stream. Sorbitol was added before extraction as an internal standard to correct for differences in extraction efficiency, subsequent differences in derivatization efficiency and changes in sample volume during heating. Dried extracts were silylated for 1 h at 70° C. to generate trimethylsilyl (TMS) derivatives, which were analyzed after 2 days with an Agilent Technologies Inc. (Santa Clara, Calif.) 5975C inert XL gas chromatograph-mass spectrometer as described elsewhere (Li Y. et al. (2012). *Biotechnol. Biofuels* 5: 2; Tschaplinski T. J., et al. (2012). *Biotechnol. Biofuels* 5: 71). Metabolite peak extraction, identification, and quantification were described previously (Tschaplinski T. J., et al. (2012). *Biotechnol. Biofuels* 5: 71), and unidentified metabolites were denoted by their retention time as well as key mass-to charge (m/z) ratios. There were 10 replicate plants of up-regulated EPSP-TF and empty vector controls from three lines each. Data were pooled across lines and treatment means were tested for statistical significance ($p<0.05$) using Student's t-tests.

Structural Modeling and Molecular Dynamics Simulations

PtrEPSP-TF and PtrEPSP-SY models were built using the iterative threading assembly refinement (I-TASSER, v3.0) protein structure modeling toolkit (Roy A et al. (2010). *Nat. Protoc.* 5: 725-738), which integrates the ab initio (free) modeling and template-based modeling on the basis of the multiple threading alignments for protein structure building (Zhang Y. (2014). *Proteins* 82 (suppl. 2): 175-187). Structure-based functional annotations and ligand/cofactor predictions of the constructed models were carried out using COFACTOR (Roy A. et al. (2012) *Nucleic Acids Res.* 40: W471-W477). The structure-based phylogenetic analysis was performed using the MultiSeq (Roberts E. et al. (2006). *BMC Bioinformatics* 7: 382) bioinformatics toolkit embedded in Visual Molecular Dynamics (VMD) (Humphrey W. et al. (1996). *J. Mol. Graph.* 14: 33-38, 27-28). A 200-ns molecular dynamics (MD) simulation without any restraint was performed for the best model constructed by I-TASSER. The online program MolProbity (Chen V. B. et al., (2010). *Acta Crystallogr. D Biol. Crystallogr.* 66: 12-21) was applied to validate the rotamers of Asn, Gln and His, and to determine the protonation states of titratable residues of Glu, Asp, Lys, Arg and His. Missing hydrogen atoms were added using the HBUILD module in CHARMM (Brooks B. R., et al. (2009). *J. Comput. Chem.* 30: 1545-1614). A water box with at least 15 Å to the edge of the protein was used, and sodium/chloride ions were added to balance the net charge of the whole system. The MD simulations were performed using the software NAMD (Phillips J. C. et al. (2005). *J. Comput. Chem.* 26: 1781-1802). The CHARMM protein force field (Best et al., 2012) and TIP3P water model (Jorgensen W. L. et al. (1983). *J. Chem. Phys.* 79: 926-935) were adopted in all MD simulations. A time step of 2-fs was applied with the SHAKE algorithm to fix the bonds involving hydrogen atoms. In each MD simulation, after a 50,000-step energy minimization, the temperature of the system was gradually heated to 300 K at a rate of 0.001 K per time step. The MD simulations were performed under the constant-temperature, constant-pressure (NPT) ensemble with the system pressure of 1 atm and temperature of 300 K maintained by the Langevin piston controls. Cutoff of switching between 9 and 11 Å was applied for the non-bonded interactions, and particle mesh Ewald summation with a grid spacing of 1.35 Å was applied for long-range electrostatic interactions, respectively. For each of the 200 ns MD simulations, analyses were carried out on the last 100 ns of all MD trajectories.

EPSP Synthase Activity

The enzymatic activities of purified PtrEPSP-TF and PtrEPSP-SY were assayed in 100 μl of 150 mM HEPES-NaOH (pH 7.0), 2 mM DTT, 100 mM KCl, 1 mM PEP (Sigma), and 1 mM S3P (Sigma). After incubating the samples at room temperature for 10 min, the enzymatic activity was then determined by measuring the amount of inorganic phosphate using malachite green. The enzymatic activity (U/mg) represents μmol product/min of reaction/mg of EPSP protein. For each sample, three reactions were performed in parallel to calculate the mean value and standard deviation (error bar), which were used in Student's t-tests.

Subcellular Localization in *Populus* Protoplasts

Protoplasts from *Populus* were isolated and subsequently transfected, as previously described (Guo et al., 2012). For EPSP subcellular localization, 8 μg of YFP fusion PtrEPSP-TF, PtrEPSP-SY, and PtrhAT constructs (Cauliflower mosaic virus (CaMV) 35S promoter driving) were co-transfected with 2 μg of VirD2NLSmCherry construct (Nuclear marker) into 100 μl of protoplasts, respectively. After 12 h incubation, YFP and mCherry fluorescence were examined and photographed. Images were collected on a Zeiss LSM 710 confocal microscope and images were processed using the Zeiss ZEN software package.

Transcriptional Activity Assay

The protoplast transfection-based transcriptional activity assay was performed according to a previously described method (Tiwari et al., 2003). Ten micrograms of effector, reporter, and/or transactivator plasmids were co-transfected into 100 μl of *Populus* protoplasts using the PEG-calcium transfection method and incubated under darkness for 18-20 h at room temperature. A GUS activity assay was performed as described (Yoo et al., 2007). GUS activity was measured using a Fluoroskan microplate reader. To normalize GUS activity, 100 ng of 35S:Luciferase plasmid was co-transfected for each transfection. Luciferase activity was measured using a Promega Luciferase Assay System according to the manufacturer's manual. All transfections were performed in triplicate to calculate the mean value and standard deviation (error bar), which were used in Student's t-tests.

Electrophoretic Mobility Shift Assay

PtrEPSP-TF (full-length and truncated fragments) and PtrEPSP-SY were cloned into the pGEX-6P-1 vector (GE Healthcare) by BamHI and EcoRI for GST fusion constructs. PtrhAT was cloned into the pGEX-6P-1 vector by EcoRI and XhoI. The constructs were transformed into *E. coli* strain BL21(DE3)pLysS (Invitrogen) for protein expression. GST fusion proteins were extracted and purified as previously described using Glutathione Sepharose 4B beads (GE Healthcare) (Xie et al., 2012). To perform EMSA, GSTPtrEPSP-TF (full-length and truncated fragments) and GST-PtrEPSP-SY were then eluted from beads by incubating with Elution Buffer (50 mM Tris-HCl pH 8.0, 10 mM reduced glutathione) at 4° C. for 30 min. PtrhAT was cleaved from beads by PreScission Protease (GE Healthcare) in Cleavage Buffer (50 mM Tris-HCl, 150 mM NaCl, 1 mM EDTA, 1 mM DTT, pH7.0) at 4° C. overnight. For DNA probes, DNA fragments inside the region 500-bp upstream from the start codon were amplified by PCR from Populus clone 717-1B4 (female, *Populus tremula* x alba) genomic DNA, gel purified, and end labeled with biotin using a DNA 3' End Biotinylation Kit (Thermo Scientific) according to the manufacturer's manual. The DNA binding reaction included 0.25 nM Biotin-labeled probe, 0.4 µg of purified protein, 10 mM Tris-HCl (pH 7.5), 50 mM KCl, 1 mM DTT, 2.5% Glycerol, 5 mM $MgCl_2$, 1 µg Poly (dI-dC), 0.05% NP-40. Reactions were incubated at room temperature for 20 min. The reaction mixtures were then resolved in a 6% DNA retardation gel (Novex) by electrophoresis at 100 V for 1-2 h and electrophoretically transferred to Nylon membrane. Signals of biotin were detected using the Chemiluminescent Nucleic Acid Detection Module (Thermo Scientific) as suggested by the manufacturer.

Micro-Chromatin Immunoprecipitation (µChIP) in *Populus* Protoplasts

µChIP was performed as previously described with a few modifications (Dahl and Collas, 2008; Para et al., 2014). Myc fusion PtrEPSP-TF and PtrhAT were transfected and transiently expressed in protoplasts. After 14 h incubation at room temperature, approximately 50,000 transfected protoplasts were then used for µChIP. Cells were crosslinked by 1% formaldehyde in W5 Solution (154 mM NaCl, 125 mM $CaCl_2$, 5 mM KCl, 2 mM MES pH 5.7) for 8 min at room temperature with a gentle rotation. The formaldehyde was subsequently quenched by adding 1.25 M glycine (Sigma-Aldrich) to the final concentration of 125 mM and incubating the samples for 5 min at room temperature with gentle rotation. After two washes with W5 Solution, cells were collected by centrifugation (2000 rpm for 10 min, 4° C.) and lysed in 50 µl of Lysis Buffer (50 mM Tris-HCl pH 8.0, 100 mM NaCl, 10 mM EDTA pH 8.0, 1% SDS, 1 mM PMSF, and protease inhibitor (Sigma-Aldrich)) with intermittent vortexing for 20 min. The concentration of SDS was then diluted to less than 0.1% by adding 800 µl of ChIP Dilution Buffer (0.01% SDS, 1.1% Triton X-100, 1.2 mM EDTA, 16.7 mM Tris-HCl pH 8.0, 167 mM NaCl, 1 mM PMSF, and protease inhibitor (Sigma-Aldrich)). After dilution, cell lysate was sonicated for 150 s with 0.7 s 'On' and 1.3 s 'Off' pulses at 20% power amplitude using the Branson 450 Digital sonifier machine to achieve chromatin fragments of 150-600 bp (Adli and Bernstein, 2011). The sonicated cell lysates was added to an additional 150 µl of ChIP Dilution Buffer and centrifuged at 10,000 g for 10 min at 4° C. to remove cellular debris. After centrifugation, the supernatant was aliquoted into three clean 1.5 ml tubes: 25 µl for Input sample, 450 µl for IgG control, 450 µl for ChIP with antibody. Additional ChIP Dilution Buffer was then added: 75 µl for Input sample, 450 µl for IgG control, 450 µl for ChIP with antibody. The protein-DNA complexes were captured using anti-Myc antibody (Sigma-Aldrich) at 4° C. overnight, and then incubated with washed Magnetic Protein-A beads (GE healthcare) at 4° C. for 1 h. After six washes (two washes with Low-salt buffer (150 mM NaCl, 0.1% SDS, 20 mM Tris-HCl pH 8.0, 2 mM EDTA pH 8.0, and 1% Triton X-100), two LiCl buffer washes (0.25 M LiCl, 1% Na-deoxycholate, 10 mM Tris-HCl pH 8.0, 1% NP-40, 1 mM EDTA pH 8.0) and two TE buffer washes (10 mM Tris-HCl pH 8.0, 1 mM EDTA pH 8.0), DNAs were eluted from beads as described (Dahl and Collas, 2008). The ChIPed DNA and input DNA were then cleaned and concentrated using a Qiagen MinElute PCR Purification Kit (Qiagen). qPCR was then performed to quantify DNA enrichment. Three biological replicates were performed. The following primers were used for qPCR: Promoter~PtActin (Potri.019G010400) (F: ACCTACTTCGTTTGGTCAT-TGTTA (SEQ ID NO: 17), R: CAAATACAACAT-ACTAGTTCCTCCAC (SEQ ID NO: 18)); Promoter~PtrhAT (Potri.016G026100) (F: CCCACAACAATCA-ACCCATA (SEQ ID NO: 19), R: GGGGAAAATAAGG-GAAAAAGG (SEQ ID NO: 20)); Promoter~PtrMYB021 (Potri.009G053900) (F: TGAGCAGTAAAACGGTTTGG (SEQ ID NO: 21), R: GGAAAAGGACAAGATCATGGA (SEQ ID NO: 22)). µChIP analyses were performed in triplicate using independent transfected cells to ensure results were consistent.

RNA-Seq Analysis

For each transgenic line, mature stems (internodes 6 to 8) were collected between 12:00 PM and 2:00 PM from four individual plants growing in the greenhouse for six months after propagation from cuttings. Total RNAs were extracted from the developing xylem (scrapped stem under the bark of the mature stem (internodes 6 to 8)). Stranded RNASeq library(s) were created and quantified by qPCR. Sequencing was performed using an Illumina HiSeq-2500 instrument. Raw fastq file reads were filtered and trimmed using the JGI QC pipeline resulting in the filtered fastq file (*.anqrp.fastq.gz files). Using BBDuk (BBDuk Sourcefoge website), raw reads were evaluated for artifact sequence by k-mer matching (k-mer=25), allowing 1 mismatch and detected artifact was trimmed from the 3' end of the reads. RNA spike-in reads, PhiX reads and reads containing any Ns were removed. Quality trimming was performed using the phred trimming method set at Q6. Finally, following trimming, reads under the length threshold were removed (minimum length 25 bases or ⅓ of the original read length, whichever is longer). Raw reads from each library were aligned to the reference genome using TopHat (Kim et al., 2013a) with only unique mapping allowed (BAMs/directory). If a read mapped to more than one location, it was ignored. FeatureCounts (Liao et al., 2014) was used to generate the raw gene counts. Raw gene counts were used to evaluate the level of correlation between biological replicates using Pearson's correlation and to determine which replicates would be used in the DGE analysis. DESeq2 (v1.2.10) (Love et al., 2014) was subsequently used to determine which genes were differentially expressed between pairs of conditions. The parameters used to call a gene DE between conditions were $p<0.05$.

qPCR Analyses

RNA extraction and gene expression: RNA was extracted from stem and shoot tip samples using Plant RNA extraction kit (Sigma, St Louis, Mo.) with modifications as described in a previous report from the inventors (Payyavula et al., 2014). cDNA synthesis was performed using DNAse free total RNA (1.5 µg), oligo dT primers and RevertAid Reverse Transcriptase (Thermofisher). Reverse transcription quantitative PCR (RT-qPCR) was performed using 3 ng cDNA, 250 nM gene-specific primers and iTaq Universal SYBR Green Supermix (Bio Rad). Gene expression was calculated by the delta-delta cT method (Livak and Schmittgen, 2001) using the expression of housekeeping genes (18S ribosomal RNA and Ubiquitin-conjugating enzyme E2) for template normalization. The following RT-qPCR primers were used: PtrEPSP-TF (F: ACCTGAGATCGTTTTGCAACC (SEQ ID NO: 23), R: CAACAGTCGTACCCTCAGAGA (SEQ ID NO: 24). Total RNAs were extracted from root, young leaf (1-3rd from apex), mature leaf (4-6th from apex), senescent leaf (yellow leaf), young stem (internodes 1 to 3), mature stem (internodes 6 to 8), petiole of mature leaf, phloem (bark of mature stem) and developing xylem (scrapped stem under bark of mature stem) to analyze the expression of PtrEPSP-TF in various tissue and organs. RT-qPCR analyses were performed using samples from three individual plants to ensure results were consistent.

Phylogenetic Tree Construction

Hmmer (v3.1) (Eddy, 2011) was used to identify PtrEPSP-TF homologs using the EPSP domain training file obtained from Pfam (Finn et al., 2006) in all species from Phytozome (Phytozome website) except Salix. Suchowensis, which was obtained from the willow genome website (Dai et al., 2014). Multiple alignment analysis of these EPSP genes was carried out using Muscle (version 3.8) (Edgar, 2004) at the amino acid level with default settings. Amino acid alignments were translated into nucleotide alignments using ad hoc perl scripts. The phylogenetic tree of the EPSP gene family was constructed by Mrbayes (v3.2.2) (Ronquist and Huelsenbeck, 2003) using the Bayesian inference method with substitution model set as GTR+I+F and a Markov Chain Mont Carlo (MCMC) set as 1,000,000 generations.

Populus DAYSLEEPER like genes were identified by searching for sequence similarity to the Arabidopsis DAYSLEEPER (AT3G42170) amino acid sequence in the Populus V3.1 reference genome assembly. After multiple sequence alignment using Clustal X2.1, the unrooted tree was generated using the neighbor-joining method with 1000 bootstrap replicates with MEGA 5.1 software.

Cell Fractionation and Protein Gel Blots

One milliliter of transfected protoplasts ($2 \times 10^5$ ml$^{-1}$) was incubated at room temperature for 14 h for protein expression and then collected by centrifugation at 2000 rpm for 10 min at 4° C. The non-nuclear and nuclear fractions were separated according to a previously published method (Yin et al., 2016). Total proteins were extracted by incubating protoplasts in extraction buffer (20 mM Tris-HCl pH 7.4, 25% glycerol, 20 mM KCl, 2 mM EDTA, 2.5 mM MgCl2, 250 mM sucrose, 1 mM DTT, and 1 mM PMSF) for 1 h at 4° C. After centrifugation at 1,500×g for 10 min at 4° C., the clear supernatant was taken and enriched using acetone precipitation as the non-nuclear fraction. The pellet was washed twice with nuclei resuspension Triton buffer (20 mM Tris-HCl pH 7.4, 25% glycerol, 2.5 mM MgCl2, 0.2% Triton X-100) and once with nuclei resuspension buffer (20 mM Tris-HCl pH 7.4, 25% glycerol, 2.5 mM MgCl2). Non-nuclear and nuclear proteins were separated by SDS/PAGE and transferred to polyvinylidene difluoride (PVDF) membrane (Bio-rad). Anti-Myc (Sigma, C3956), anti-histone H3 (Abcam, ab1791), and anti-UGPase (Agrisera, AS05 086) were used as primary antibodies. Anti-Rabbit IgG peroxidase antibody (Sigma, A9169) were used as secondary antibodies. Chemiluminescent signals were generated by using the ECL Immunoblotting Detection Reagents (GE Health) and detected with ChemiDoc XRS+ system (Bio-Rad).

Accession Numbers and Seqeunces

Sequence data from this disclosure can be found in the GenBank/EMBL data libraries under accession numbers: PtrEPSP-TF, XM_002301243; PtrEPSP-SY, XM_024584967; PtrhAT, XM_024588158; PtrMYB021, KF148678; PtWND1B, HQ215848.

TABLE 1

| Sequences from Populus balsamifera subsp. trichocarpa | |
|---|---|
| Sequence Description | |
| PtrhAT DNA sequence | SEQ ID NO: 1 |
| PtrhAT protein sequence | SEQ ID NO: 2 |

TABLE 1-continued

| Sequences from Populus balsamifera subsp. trichocarpa | |
|---|---|
| Sequence Description | |
| PtrEPSP-TF DNA sequence | SEQ ID NO: 3 |
| PtrEPSP-TF protein sequence | SEQ ID NO: 4 |
| PtrEPSP-SY DNA sequence | SEQ ID NO: 5 |
| PtrEPSP-SY protein sequence | SEQ ID NO: 6 |
| PtrMYB021 DNA sequence | SEQ ID NO: 7 |
| PtrMYB021 protein sequence | SEQ ID NO: 8 |
| PtWND1B DNA sequence | SEQ ID NO: 9 |
| PtWND1B protein sequence | SEQ ID NO: 10 |

Example 2: SNPs in the Potri.002G146400 Gene Have Significant Associations with Lignin Content in Populus In a study designed to assess the genetic basis of lignin biosynthesis across multiple environments in Populus, the inventors utilized the Populus association mapping panel characterized for lignin content in two different environments. Wood samples were taken from 1,081 mature P. trichocarpa genotypes in 2008 across the species range as the association mapping panel was assembled (Muchero et al., 2015). Subsequently, the same panel of genotypes was established in a field site in Clatskanie, Oreg. in 2009 and wood samples were obtained in July 2012. Phenotyping results for these samples were published previously (Muchero et al., 2015). To identify SNP markers associated with lignin content, the inventors targeted chromosome II, which was previously shown to harbor major QTLs for lignin content and syringyl-to-guaiacyl ratio (S/G) (Yin et al., 2010). Genotype-to-phenotype correlations were performed using 2,352 SNPs selected for even coverage on chromosome II. This analysis revealed that multiple SNPs within a 4.2 Kb interval exhibited associations with lignin content across two environments ranking 4th, 5th, 7th and 8th in the native environment from where the parent trees were sampled. Three of the same four SNPs ranked 1st, 6th and 7th out of the 2,352 markers in the Clatskanie field site when four-year old clones were sampled and assessed for lignin content. These SNPs fell within a Populus gene model, POPTR_0002s14740 (Potri.002G146400, v.3.1) annotated as a 5-enolpyruvylshikimate 3-phosphate (EPSP) synthase (scaffold_2_10944029 (C/T) intron, scaffold_2_10945723 (A/G) intron, scaffold_2_10947571 (A/C) non-coding region and scaffold_2_10948215 (G/T) noncoding region). The fact that this interval exhibited association with lignin content in decades-old mature trees in their native environments across the species range as well as juvenile 4-year-old trees suggested that this locus might play a key role in lignin biosynthesis in Populus. To rule out the possibility of false associations due to the low frequency of these alleles, Potri.002G146400 overexpression Populus was generated and analyzed for phenotypic and molecular changes related with lignin biosynthesis.

Example 3: Overexpression of Potri.002G146400 Alters the Deposition of Lignin, Accumulation of Phenylpropanoid Metabolites, and Expression of Secondary Cell Wall Biosynthesis Genes To experimentally link the Potri.002G146400 locus with lignin biosynthesis, first, lignin deposition was investigated in stem sections from one-month-old transgenic Populus overexpressing Potri.002G146400. Lignin depositions of two independent transgenic lines (Potri.002G146400 OX-1 and Potri.002G146400 OX-2) were compared with that of plants transformed with empty vector (control). Phloroglucinol-HCl staining was performed to visualize lignin in cell walls (redviolet). In Potri.002G146400 overexpression plants, the inventors observed ectopic deposition of lignin in epidermis, phloem fiber, and pith cells (FIG. 1A), suggesting that Potri.002G146400 affects lignin biosynthesis in *Populus*.

Figure 1B:
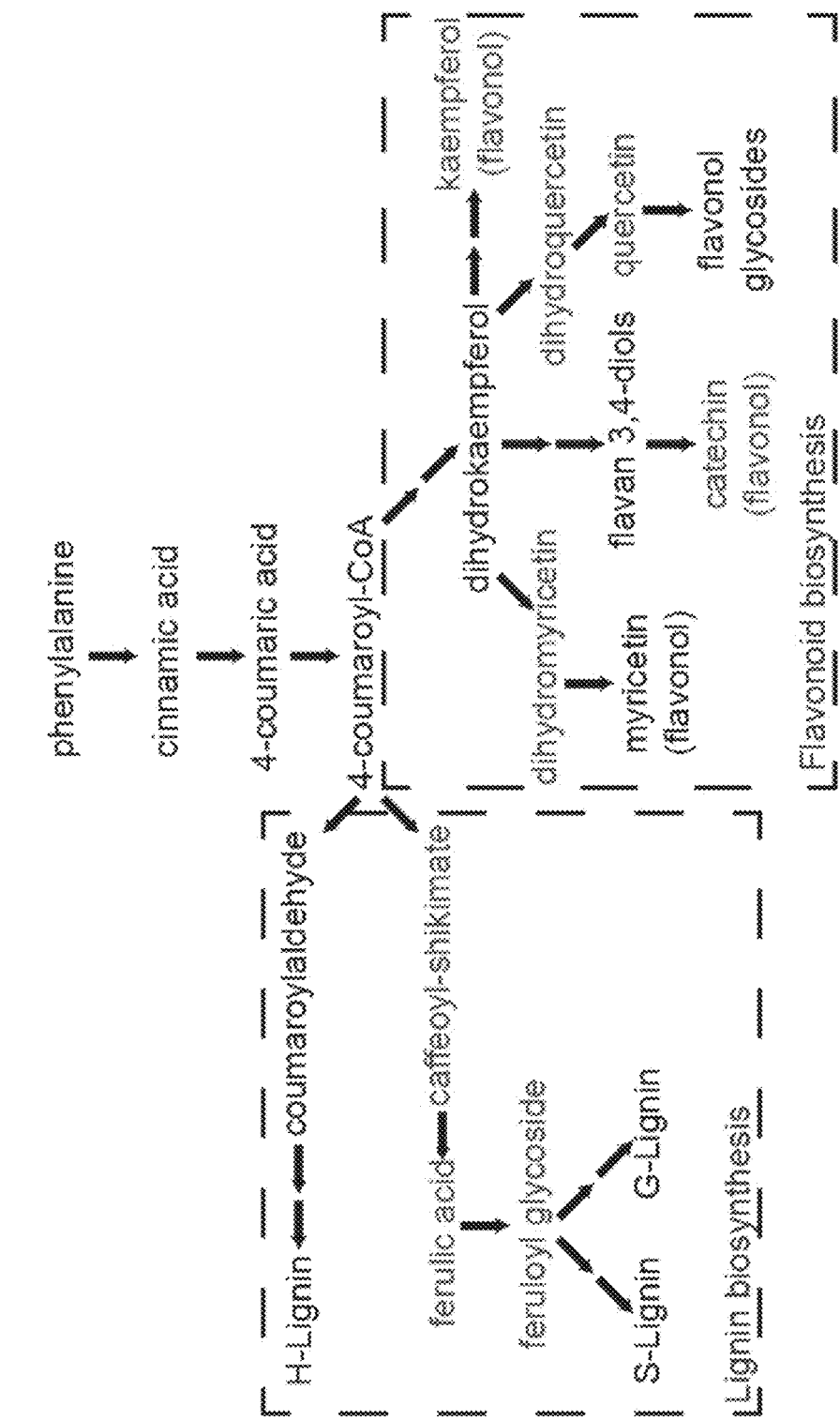

To provide further evidence supporting the connection between PtrEPSP-TF and lignin biosynthesis, secondary metabolites were measured in Potri.002G146400 overexpression lines using gas chromatography mass spectrometry (GC-MS). Metabolites in the lignin biosynthesis pathway, including feruloyl glycoside, ferulic acid, and caffeoyl conjugates, exhibited significant increases, between 7% and 87%, in the overexpression plants relative to controls (FIG. 1B). Besides lignin-related metabolites, other products of the phenylpropanoid pathway also showed increased accumulation. As shown in FIG. 1B, levels of quercetins, dihydromyricetin and catechins exhibited up to 2.8-fold increases in the overexpression lines.

To fully define the molecular effects of Potri.002G146400 in *Populus*, total RNAs were extracted from stems of transgenic *Populus* plants and RNA-seq analysis was performed. Differential gene expression (DGE) analysis identified a total of 89 genes, which had consistent expression changes between two independent Potri.002G146400 overexpression lines. Based on DGE analysis performed using DESeq2 (v1.2.10) (Love et al., 2014), 71 up-regulated genes and 18 downregulated genes were identified (P value <0.01, false discovery rate [FDR] <0.05; Table S2). This set was too small for Gene Ontology (GO) enrichment. By searching biological functions of individual gene, a number of secondary cell wall biosynthesis genes were identified among upregulated genes: Potri.006G087100 (LACCASE 17), Potri.006G087500 (LACCASE 17), and Potri.006G096900 (LACCASE 4) for lignin biosynthesis; Potri.009G006500 (IRX7) and Potri.011G132600 (IRX8) for xylan biosynthesis; and Potri.011G058400 (SND2, which directly activate CesA8 (cellulose), but not IRX9 (xylan) or 4CL1 (lignin) in *Arabidopsis* (Zhong et al., 2008)) for cellulose biosynthesis. More importantly, the expression of two master regulators of secondary cell wall biosynthesis, including Potri.009G053900 (PtrMYB021/MYB46) and Potri.011G153300 (NAC SECONDARYWALL THICKENING PROMOTING FACTOR 1, NST1) (Mitsuda et al., 2007), were up-regulated by Potri.002G146400 overexpression. By contrast, the 18 down-regulated genes exhibit little association with secondary cell wall biosynthesis.

Based on these cumulative observations, the inventors hypothesized that Potri.002G146400 may affect lignin biosynthesis and the phenylpropanoid pathway via regulating the expression of master regulators of secondary cell wall biosynthesis, such as MYB46 and NST1.

Figure 2A:
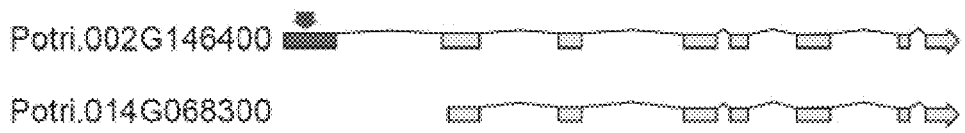
FIGS. 2A-2E. Potri.002G146400 encodes an HTH motif containing protein. (A) Comparison of two putatively paralogous genes Potri.002G146400 and Potri.014G068300 shows an additional exon red) encoding an N-terminus helix-turn-helix motif. (B) Left panel: Purified GST, GST-Potri.002G146400, and GST-Potri.014G068300 were resolved on an SDS-PAGE gel and stained with Coomassie Blue. The protein molecular weights are indicated on the left. GST only was used as a negative control. Right panel: EPSP synthase activities of GST, GST-Potri.002G146400, and GST-Potri.014G068300. For each sample, three reactions were performed in parallel to calculate the mean value and standard deviation (error bar), which were used in Student's t-tests (* $P<0.001$,  $P<0.01$, * $P<0.05$, ns $P>0.05$). (C) Left panel: Potri.002G146400 (yellow) superimposed on an EPSP synthase from the *Agrobacteria tumefaciens* strain CP4 crystallographic structure (gray, PDB entry 2GG6) bound with a shikimate-3-phosphate substrate (blue and red spheres). The HTH domain is shown in red. Right panel: a detailed view of the HTH domain of Potri.002G146400 comprised of three characteristic α-helices H1 to H3, which are surrounded by β-sheets B1 to B3 in the enzyme. The rest of the enzyme is shown in ribbons. (D) Subcellular localization of Potri.002G146400-YFP and Potri.014G068300-YFP in *Populus* protoplasts (green). The nuclear marker mCherry-VirD2NLS is shown in red. Scale bar: 10 µm. (E) Immunoblot showing the accumulation of Potri.002G146400-Myc in non-nuclear and nuclear fractions. Potri.002G146400-Myc and Potri.014G068300-Myc were blotted using anti-Myc. UGPase and histone H3 were blotted to indicate the purity of non-nuclear and nuclear fractions, respectively. Non-N, non-nuclear fraction; N, nuclear fraction. P value comparison is calculated using two-tailed Student's t-tests (* $P<0.001$,  $P<0.01$, * $P<0.05$, ns $P>0.05$).

Example 4: Potri.002G146400 Encodes an EPSP Synthase Protein with an Additional Motif at its N-Terminus In *Populus*, Potri.002G146400 has one paralog Potri.014G068300 that, presumably, arose from the Salicoid whole-genome duplication event (Tuskan et al., 2006). Both are annotated as EPSP synthases. Based on RNA-seq coverage, Potri.002G146400 has a longer N-terminal than Potri.014G068300. Although the proteins encoded by these two genes share 90.0% sequence similarity, Potri.002G146400, the candidate gene, carries an extra exon in the 5' region, resulting in a longer cDNA transcript with a total of 1,557 nucleotides and encoding a protein with 518 amino acids (~56 kDa), which is larger than the canonical EPSP synthase (~46 kDa) (FIG. 2A). By contrast, the transcript for the putative paralog Potri.014G068300 is 1,173 nucleotides long and encodes a protein with 390 amino acids, corresponding to the canonical EPSP sequences reported in multiple organisms (Garg et al., 2014).

Figure 2B:
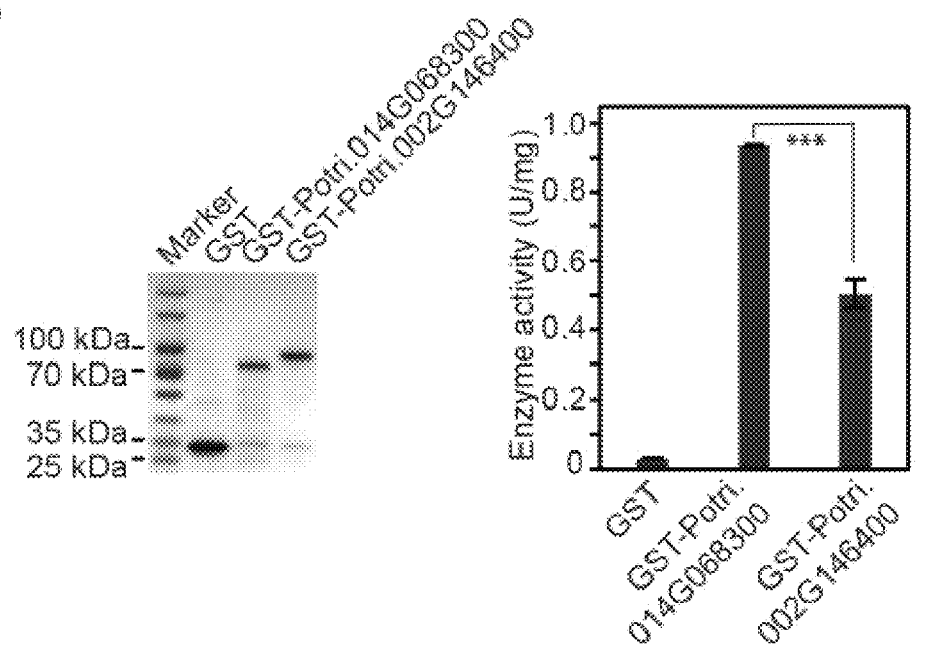

To determine whether the two putative *Populus* paralogs retain EPSP synthase activity, GST-tagged proteins were expressed in *E. coli* and purified (GST-Potri.002G146400 and GSTPotri. 014G068300; FIG. 2B). A GST tag-only was purified as a negative control. EPSP synthase activity was measured with the presence of 1 mM phosphoenolpyruvate (PEP), 1 mM shikimate-3-phosphate (S3P), and 100 mM KCl. As shown in FIG. 2B, both Potri.002G146400 (0.506±0.041 U/mg) and Potri.014G068300 (0.936±0.003 U/mg) displayed enzymatic activities. The shorter paralog (Potri.014G068300) exhibited stronger EPSP synthase activity than the longer paralog (Potri.002G146400; FIG. 2B).

Figure 2C:
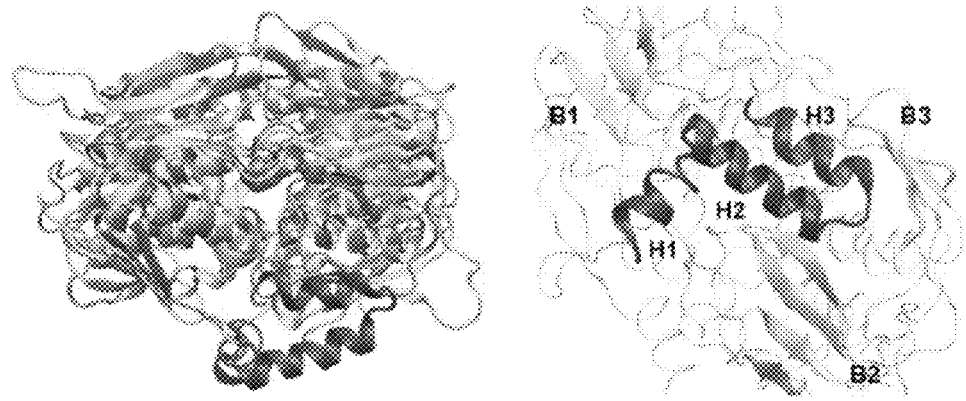

Given the sequence variation between EPSP synthase paralogs, atomistic modeling and molecular dynamics simulations were employed to characterize differences between the two *Populus* paralogs. Characterization of the tertiary structure ascending from the longer N-terminus revealed a putative helix-turn-helix (HTH) motif spanning amino acid residues 30-70 of Potri.002G146400 (FIG. 2C).

This motif has the classic three α-helices surrounded by three β-sheets that are characteristically found in nucleic acid-binding HTH domains of transcription factors (Aravind et al., 2005). The remainder of the protein, like the paralog Potri.014G068300, shared high similarity with the *Agrobacterium tumefaciens*-derived cp4 EPSP synthase with an intact substrate binding domain (FIG. 2C). Given that EPSP synthase, as the name implies, was only known as a biosynthesis enzyme catalyzing reactions in chloroplasts, the presence of a predicted DNA-binding domain in Potri.002G146400 suggested the possibility of an evolved or co-opted novel function.

Example 5: Protein Encoded by Potri.002G146400 Accumulates in the Nucleus

Figure 2D:
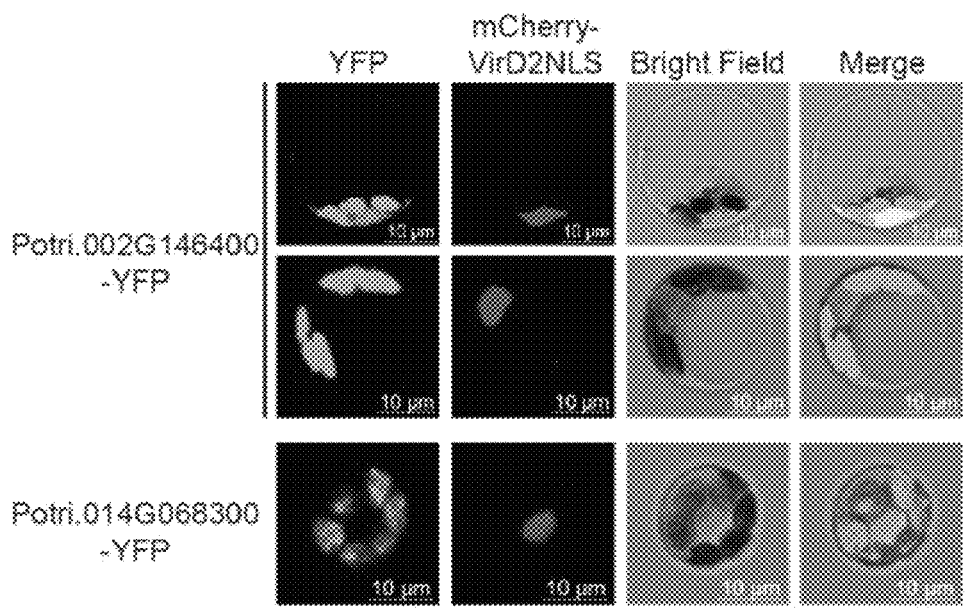
Figure 2E:
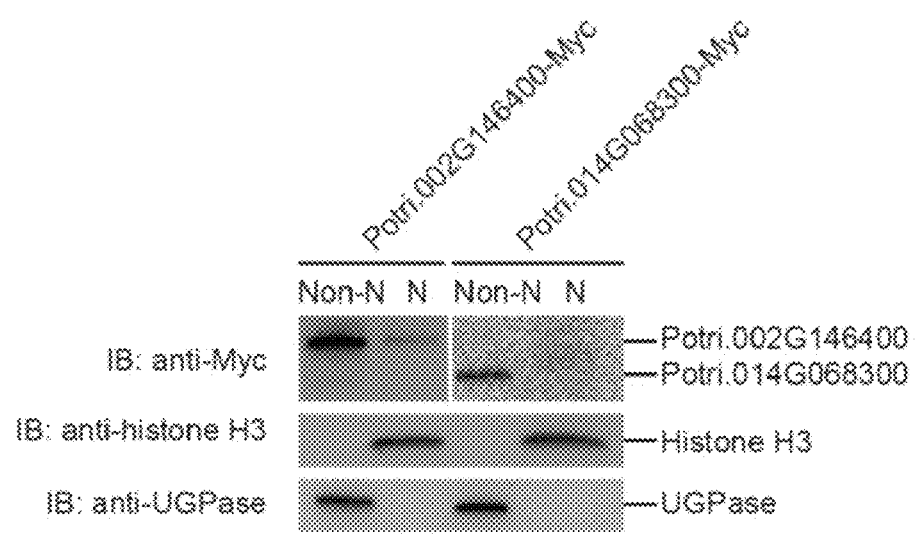

The presence of a putative HTH motif in the protein encoded by Potri.002G146400 suggested that it may have novel or additional functions divergent from the canonical EPSP synthase in the shikimate pathway. Because the molecular function of a protein is closely linked to its subcellular localization (Lu and Hunter, 2005) and to explore potential functions of Potri.002G146400, the inventors evaluated Potri.002G146400 subcellular localization using *Populus* protoplasts. The inventors generated the construct of Potri.002G146400 fused to yellow fluorescence protein (YFP) at its C-terminus (Potri.002G146400-YFP), and co-transfected it with a nuclear marker fused with mCherry tag (mCherry-VirD2NLS) (Lee et al., 2008) into *Populus* protoplasts (FIG. 2D). Although the majority of Porti.002G146400-YFP signal (shown in green) was detected in chloroplasts, the inventors observed that in approximately 10% transfected cell, the fluorescence signal of Potri.002G146400-YFP overlapped with that of mCherry-VirD2NLS. To further determine the accumulation of EPSP synthase encoded by Pori.002G146400 in the nucleus, the inventors expressed C-terminal Myc-tagged Potri.002G146400 (Potri.002G146400-Myc) in protoplasts and performed cell fractionation analysis. Immunoblotting with anti-Myc was used to detect the accumulation of Potri.002G146400-Myc in non-nuclear and nuclear fractions. The cytosolic marker UGPase and nuclear marker histone H3 were blotted simultaneously to indicate the purity of each fraction (FIG. 2E). Consistent with subcellular localization results, Potri.002G146400 accumulation was detected in both non-nuclear and nuclear fractions, whereas the homologous construct Potri.014G068300-Myc was only detected in the non-nuclear fraction (FIG. 2E). Based on these assays, Potri.002G146400 exhibits dissimilar subcellular localization from canonical EPSP synthase and accumulates in both chloroplasts and the nucleus, leading to the hypothesis that Potri.002G146400-encoded PtrEPSP functions as a transcriptional regulator, as further described below.

Example 6: Potri.002G146400-Encoded PtrEPSP is a Transcriptional Repressor

Figures 3A, 3B, 3C:
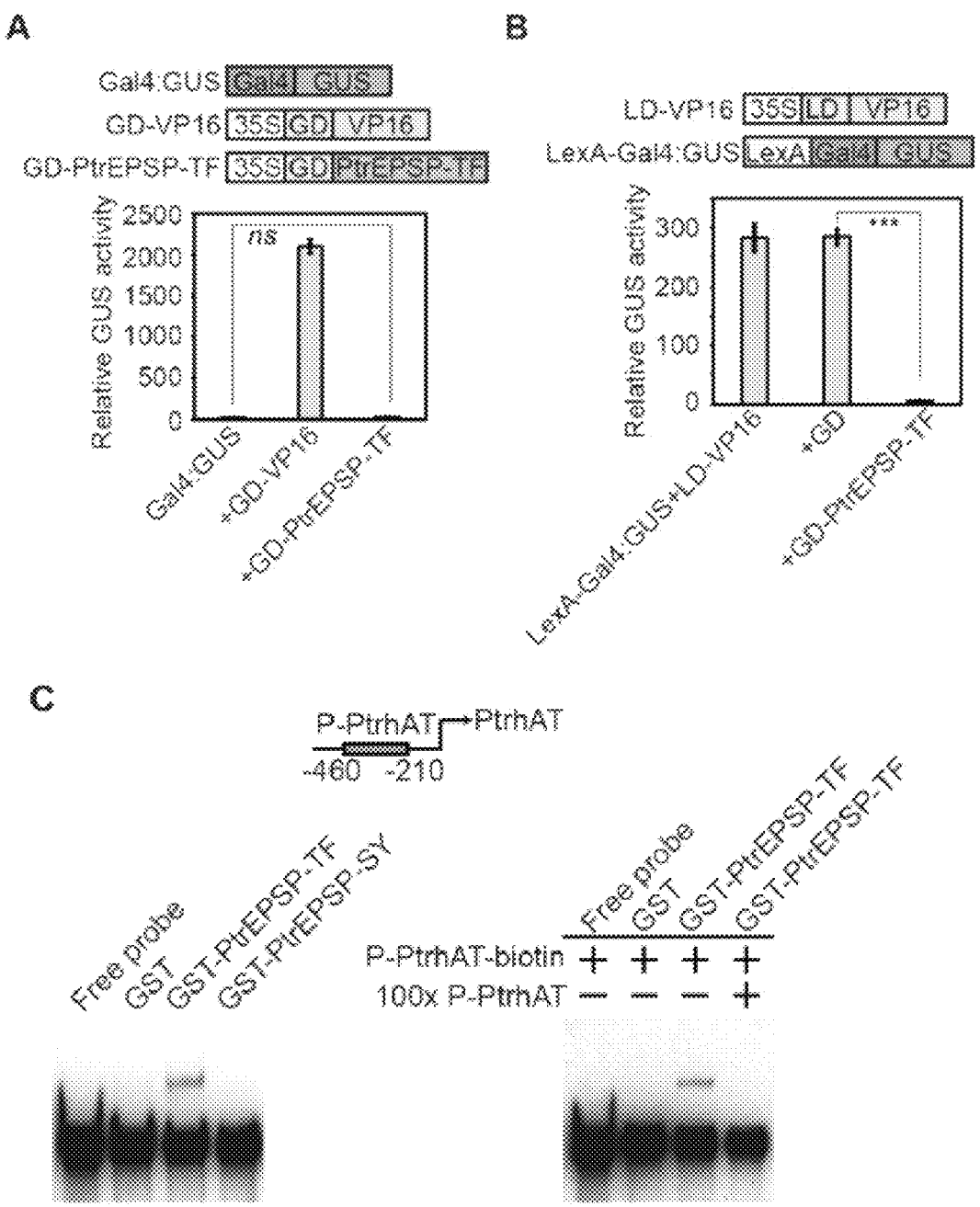
FIGS. 3A-3F. PtrEPSP-TF (Potri.002G146400) is a transcriptional repressor and directly targets PtrhAT. (A) Potri.002G146400 has no activator activity. In the reporter construct (Gal4: GUS), the GUS reporter gene was fused downstream of the Gal4 DNA binding site. The construct GD-PtrEPSP-TF was used to express Gal4 binding domain (GD) fused with PtrEPSP-TF. The construct only expressing the Gal4 binding domain (GD) was used as the negative control. Transactivator GD-VP16 was used as the positive control. (B) Potri.002G146400 represses the expression of the GUS reporter activated by the transactivator LD-VP16, in which the transcription activator VP16 is fused with LexA binding domain (LD). In the reporter construct (LexA-Gal4: GUS), the GUS reporter gene was fused downstream of the LexA DNA binding site and Gal4 DNA binding site. The construct only expressing the Gal4 binding domain (GD) was used as the negative control. Luciferase activity was used to normalize and calculate the relative GUS activity and the 35S:Luciferase construct was co-transfected with reporters and effectors. (C) DNA binding assays of PtrEPSP-TF and PtrEPSP-SY with the promoter region of PtrhAT. GST only was used as a negative control in the DNA binding assays. 100x unlabeled DNAs with the same sequence of biotin-labeled PtrhAT promoter DNA were used for the competition assay. (D) DNA binding activities of the HTH motif (PtEPSP-TF aa30-70) and truncated PtEPSP-TF without HTH motif (PtEPSP-TF aa 71-518). (E) PtrEPSP-TF binds to the PtrhAT promoter in vivo. Micro-chromatin immunoprecipitation (µChIP) was performed in protoplasts to analyze in vivo targets of PtrEPSP-TF. To quantify DNA enrichment, input DNA was analyzed by quantitative PCR to calculate ChIP signal (% INPUT). Reactions with IgG were used as negative controls. The promoter region of PtACTIN (Potri.019G010400) was amplified to indicate the specificity of ChIP. Means and standard derivations (error bars) of three technical repeats are presented. P value comparison was calculated using two tailed Student's t-tests (* $P<0.001$). µChIP was performed at least three times. (F) Transcriptional repression of PtrEPSP-TF on the PtrhAT promoter. The repression activity of the blank vector was analyzed in parallel as a negative control. For transcription activity analysis of panel A, B, and F, all transfection assays were performed in triplicate to calculate the mean value and standard deviation (error bar), which were used in Student's t-tests. P value comparison is calculated using two tailed Student's t-tests (* P<0.001, ** P<0.01, * P<0.05, ns P>0.05).

HTH motifs are commonly found in transcription factors (Aravind et al., 2005). To test whether Potri.002G146400 has transcriptional activity, the inventors applied the *Populus* protoplast transient expression system to evaluate both the transcriptional activator and repressor activity of Potri.002G146400. Constructs were generated to overexpress Gal4-DNA-binding domain-(GD)-fused Potri.002G146400 (GDPotri.002G146400, FIG. 3A). Two reporter constructs were generated to analyze activator and repressor activity. To analyze activator activity, the β-glucuronidase (GUS) reporter gene was fused downstream of the Gal4 DNA binding site (Gal4: GUS, FIG. 3A), which is bound by GD. In this assay, Potri.002G146400 was recruited to the upstream region of the GUS gene coding sequence via the association between GD and the Gal4 DNA binding site. If Potri.002G146400 acts as a transcriptional activator, one would expect the activation of the expression of GUS reporter downstream of the Gal4 DNA binding site when co-transfecting the two constructs into protoplasts. However, little GUS activity was detected in protoplasts co-transfected with GDPotri.002G146400 and Gal4: GUS (FIG. 3A). By contrast, the positive control, a construct in which GD is fused with a transactivator, the Herpes simplex virus VP16 (GD-VP16) (Tiwari et al., 2003), was capable of activating GUS reporter expression to high levels (FIG. 3A). These results suggested that Potri.002G146400 has no transcriptional activator activity.

To analyze repressor activity, a reporter construct containing the LexA DNA binding site, Gal4 DNA binding site, and GUS reporter gene was used (LexA-Gal4: GUS, FIG. 3B). The GUS expression of LexA-Gal4:GUS can be activated by a transactivator construct containing LexADNA-binding-domain-(LD)-fused VP16 (LD-VP16, FIG. 3B). GD-Potri.002G146400 and LDVP16 have different binding sites on LexA-Gal4:GUS reporter and do not compete for binding sites. When these three constructs were co-transfected into protoplasts, the GUS activity activated by LD-VP16 was abolished (FIG. 3B). As a negative control, the effector containing only GD had no effect on the expression of GUS reporter (FIG. 3B). These results demonstrated that Potri.002G146400 may function as a transcriptional repressor. As a result of this apparent transcriptional activity, hence forth Potri.002G146400 is referred to as PtrEPSP-transcription factor (PtrEPSP-TF) and Potri.014G068300 as PtrEPSP-synthase (PtrEPSP-SY).

Figure 3D:
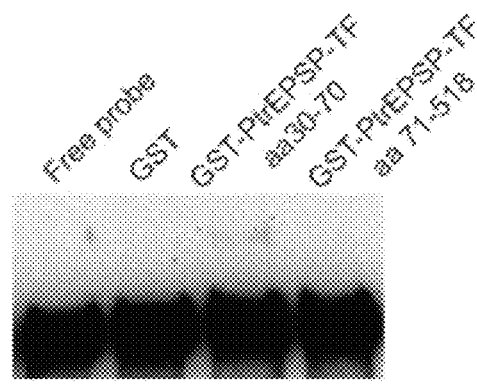

Example 7: PtrEPSP-TF Directly Binds to the PtrhAT Promoter In Vivo and In Vitro To investigate the molecular mechanisms linking the transcriptional repressor function of PtrEPSP-TF and its role in lignin biosynthesis or the phenylpropanoid pathway, the inventors sought to identify the direct target genes of PtrEPSP-TF by mining RNA-seq data from PtrEPSP-TF overexpression lines and then validating the candidates via an in vitro electrophoretic mobility shift assay (EMSA) approach. Given PtrEPSP-TF functions as a repressor in the *Populus* protoplast assays, the inventors targeted the top three genes down-regulated by PtrEPSP-TF. Among the three genes, PtrEPSP-TF, but not PtrEPSP-SY, displayed binding affinity to the promoter of a hAT transposase family gene (Potri.016G026100, designated as PtrhAT) (FIG. 3C). PtrhAT shares amino acid sequence similarity with the *Arabidopsis* DAYSLEEPER protein, which is a known global transcriptional regulator (Bundock and Hooykaas, 2005). PtrEPSP-TF does not bind to promoters of tested up-regulated genes in PtrEPSP-TF overexpression lines, such as Potri.009G053900 (PtrMYB021) and Potri.011G153300 (NST1). As shown in FIG. 3C, incubating GST-PtrEPSP-TF and biotin-labeled PtrhAT promoter (P-PtrhAT-biotin, −460 to −210) resulted in a mobility shift above the free probe band. By contrast, neither GST nor GST-PtrEPSP-SY generated the same mobility shift (FIG. 3C). Furthermore, the fact that the binding between PtrEPSP-TF and P-PtrhAT-biotin was abolished by competition with 100 times unlabeled P-PtrhAT DNA suggests that binding of PtrEPSP-TF to the PtrhAT promoter is direct and specific under in vitro conditions (FIG. 3C). To further determine whether the HTH motif in PtrEPSP-TF is responsible for the DNA binding activity, the inventors measured binding affinities of the HTH motif (PtrEPSP-TF aa30-70) and truncated PtrEPSP-TF without the HTH motif (PtrEPSP-TF aa71-518) using EMSA. As shown in FIG. 3D, it is the HTH motif that is responsible for binding to the PtrhAT promoter.

Figure 3E:
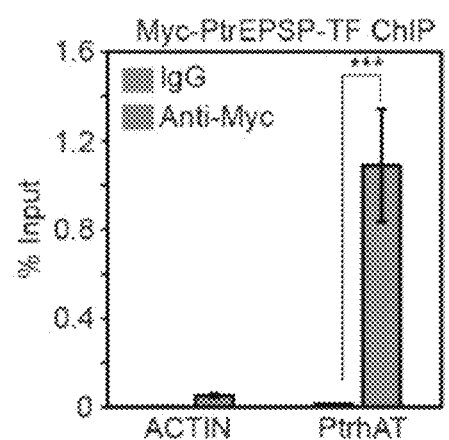

Further, chromatin immunoprecipitation (ChIP) experiments were performed to examine the in vivo binding of PtrEPSP-TF to the PtrhAT promoter. Because the generation of transgenic *Populus* is very time-consuming, the inventors combined transient protein expression technique in protoplast and micro-ChIP (µChIP) approaches modified from mammalian studies (Dahl and Collas, 2008; Para et al., 2014). µChIP is capable of discovering protein-DNA binding from limited numbers of cells, such as cell suspensions and protoplasts. The 10×Myc-tagged PtrEPSP-TF (Myc-PtrEPSP-TF) was overexpressed in Populus protoplasts and then subjected to a µChIP assay. The ChIPed DNA was analyzed by quantitative PCR to detect DNA enrichment. As shown in FIG. 3E, fragments from the PtrhAT promoter, but not from the PtACTIN promoter (Potri.019G010400) (Li et al., 2014), were enriched in Myc-PtrEPSP-TF precipitates, confirming in vivo association between PtrEPSP-TF and the PtrhAT promoter.

Figure 3F:
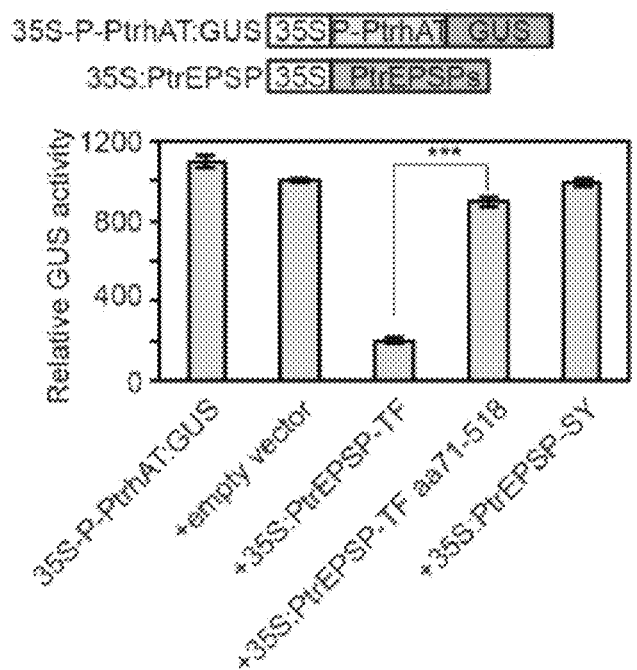

If PtrEPSP-TF directly binds to the PtrhAT promoter, as a repressor, PtrEPSP-TF is expected to suppress the activity of the PtrhAT promoter. To test this, repressor activity analysis was performed using an in vivo protoplast system. The inventors generated a construct to overexpress PtrEPSP-TF without any tag (35S:PtrEPSP-TF, FIG. 3F). In the reporter construct, the PtrhAT promoter (−460 to −210 bp from the start codon) region was inserted between the CaMV 35S promoter and GUS reporter gene (35S-P-PtrhAT: GUS, FIG. 3F). This reporter construct showed high GUS gene expression in protoplasts (FIG. 3F) whereas, co-transfection of 35S:PtrEPSP-TF and 355-P-PtrhAT:GUS showed reduced GUS expression (FIG. 3F), suggesting that PtrEPSP-TF directly binds to the PtrhAT promoter and represses its activity. Consistently, neither the truncated PtrEPSP-TF without the HTH motif (PtrEPSP-TF aa71-518) nor PtrEPSP-SY repressed the expression of GUS, which is downstream of the PtrhAT promoter (FIG. 3F).

Example 8: PtrhAT is a Transcriptional Repressor

Figures 4A, 4B, 4C:
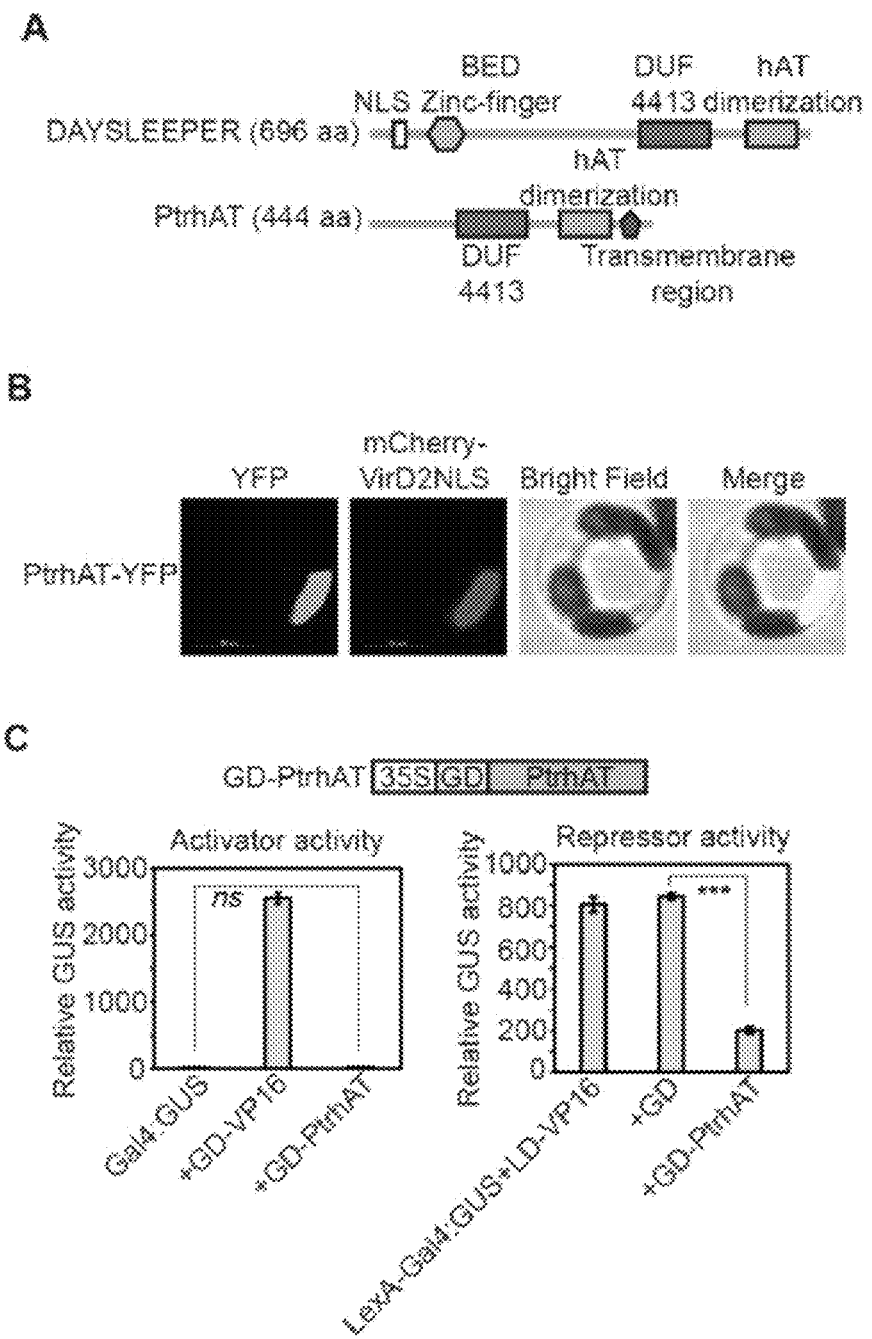
FIGS. 4A-4G. PtrhAT directly targets PtrMYB021 (Populus ortholog of MYB46). (A) Comparison of protein domains and motifs between *Populus* PtrhAT and *Arabidopsis* DAYSLEEPER. (B) Nuclear localization of PtrhAT in *Populus* protoplasts. PtrhAT-YFP (green) was transiently expressed in *Populus* protoplasts. MCherry-VirD2NLS (red) was co-transfected to indicate nucleus localization. Scale bar: 10 μm. (C) PtrhAT has repressor but not activator activity. Transcriptional activity of PtrhAT was analyzed in a similar protoplast transient expression system as the analyses on PtrEPSP-TF. 35S:Luciferase was co-transfected with reporters and effectors and Luciferase activity was used to normalize and calculate the relative GUS activity. All transfection assays were performed in triplicate to calculate the mean value and standard deviation (error bar), which were used in Student's t-tests. (D) EMSA. Left panel: Purified PtrhAT protein. GST-PtrhAT was expressed and purified in *E. coli*. The GST tag was subsequently cleaved off using PreScission Protease. Right panel: PtrhAT directly binds to the PtrMYB021 promoter in vitro. Cleavage buffer was used as the negative control in EMSA. 100× unlabeled DNAs with the same sequence of biotin-labeled PtrMYB021 promoter region were used for the competition assay. (E) μChIP shows in vivo association of PtrhAT and the PtrMYB021 promoter. Reactions with IgG were used as negative controls. The promoter region of PtACTIN was amplified to indicate the specificity of ChIP. Means and standard derivations (error bars) of three technical repeats are presented. μChIP was performed at least three times. (F) PtrhAT represses the activity of the PtrMYB021 promoter. PtrMYB021 promoter (−420 to −110 nt from the start codon) was inserted between the 35S promoter and GUS reporter and then co-transfected with vectors overexpressing PtrhAT. Blank vector was used as negative control. All transfection assays were performed in triplicate to calculate the mean value and standard deviation (error bar), which were used in Student's t-tests. (G) RT-qPCR analysis of transcript levels of PtrEPSP-TF and PtrMYB021 in two *Populus* PtrEPSP-TF RNAi lines (PtrEPSP-TF RNAi-1 and PtrEPSP-TF RNAi-2). RT-qPCR analysis was performed in triplicate to calculate the mean value and standard deviation (error bar), which were used in Student's t-tests.
Figure 6:
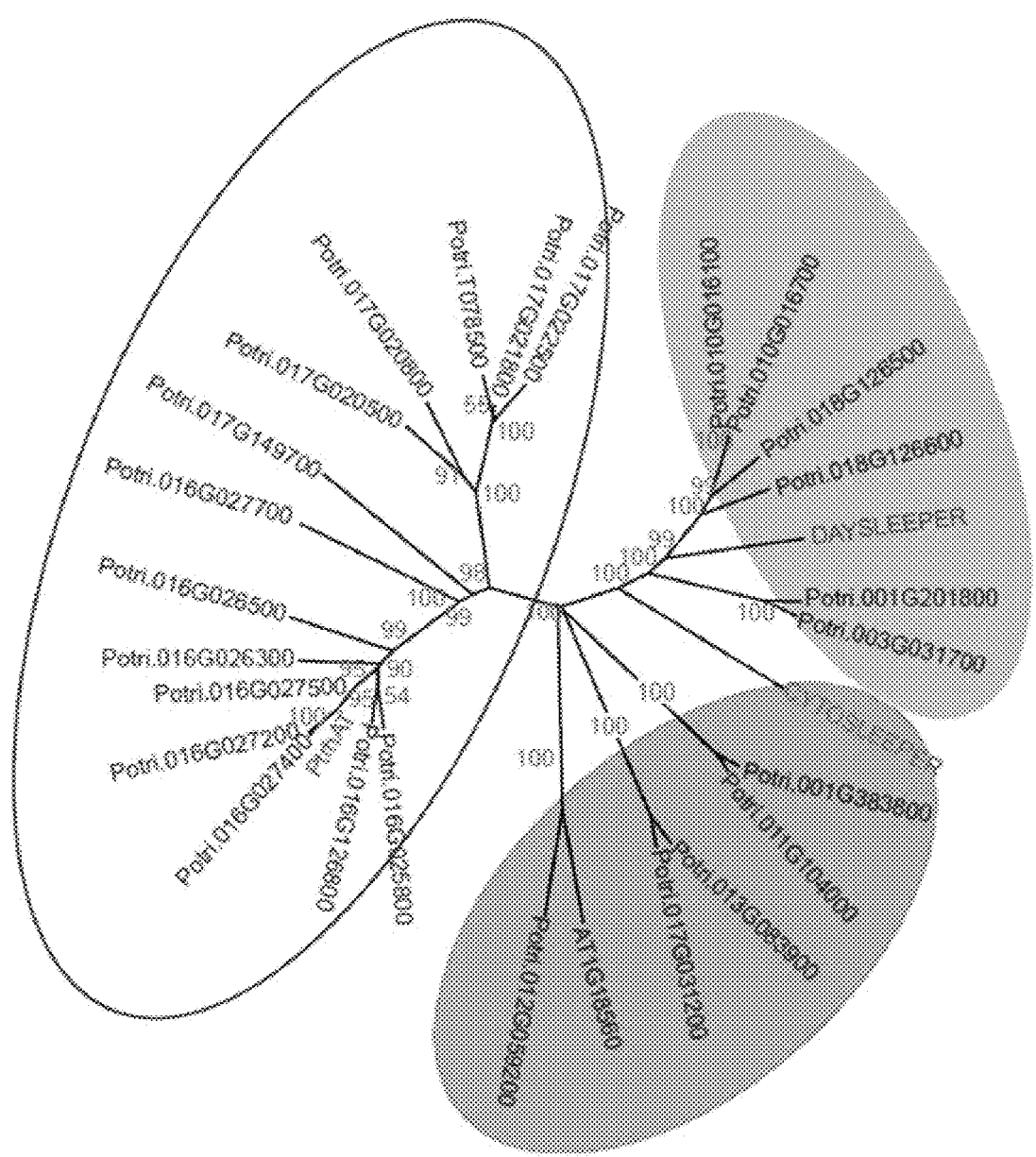
FIG. 6. Unrooted neighbor-joining phylogenies based on full-length amino acid sequences of 26 *Populus* DAYSLEEPER like proteins. Bootstrap values were given for branch node. Light gray, DAYSLEEPER subfamily; Dark gray, CYTOSLEEPER subfamily; White, third subfamily containing PtrhAT. Proteins representing each subfamily (DAYSLEEPER, CYTOSLEEPER, and PtrhAT) are indicated by red color.

Although the angiosperm-specific SLEEPER genes have been reported to be essential for plant growth and development (Bundock and Hooykaas, 2005), no direct connection has been made between SLEEPER genes and the established cell wall biosynthesis transcriptional hierarchy (Hussey et al., 2013). It should be noted that PtrhAT is much shorter than the DAYSLEEPER in *Arabidopsis* (444 aa vs. 696 aa). Amino acid alignment of PtrhAT and AtDAYSLEEPER indicated that PtrhAT also lacked the K/R rich nuclear localization domain (NLS) adjacent to the BED zinc finger domain near the N-terminal region (FIG. 4A). Because CYTOSLEEPER (encoded by AT1G15300), which also lacks the K/R rich NLS adjacent to the BED zinc finger domain, was shown to be localized in the cytosol, it has been proposed that this K/R-rich NLS domain is necessary for nuclear localization of DAYSLEEPER proteins (Knip et al., 2012). However, phylogenetic analysis of *Populus* DAYS-LEEPER-like genes illustrated that PtrhAT might not belong to either the DAYSLEEPER or CYTOSLEEPER group (FIG. 6). This prompted us to examine the subcellular localization of PtrhAT. By examining the fluorescence of PtrhAT-YFP fusion protein transiently expressed in the *Populus* protoplasts, the inventors found that PtrhAT is localized in the nucleus (FIG. 4B).

As the direct target of PtrEPSP-TF, PtrhAT appears to be an intermediary step in PtrEPSP-TF triggered transcriptional regulation. Thus, PtrhAT may also have transcriptional activity. To test this possibility, PtrhAT was fused in frame with GD (GD-PtrhAT) for transcriptional activity analyses in protoplasts. Similar to PtrEPSP-TF, GD-PtrhAT reduced GUS expression of the LaxA-Gal4:GUS reporter (activated by LD-VP16), but had no effect on GUS expression of the Gal4:GUS reporter (FIG. 4C), suggesting that PtrhAT also functions as a transcriptional repressor.

Figure 4D:
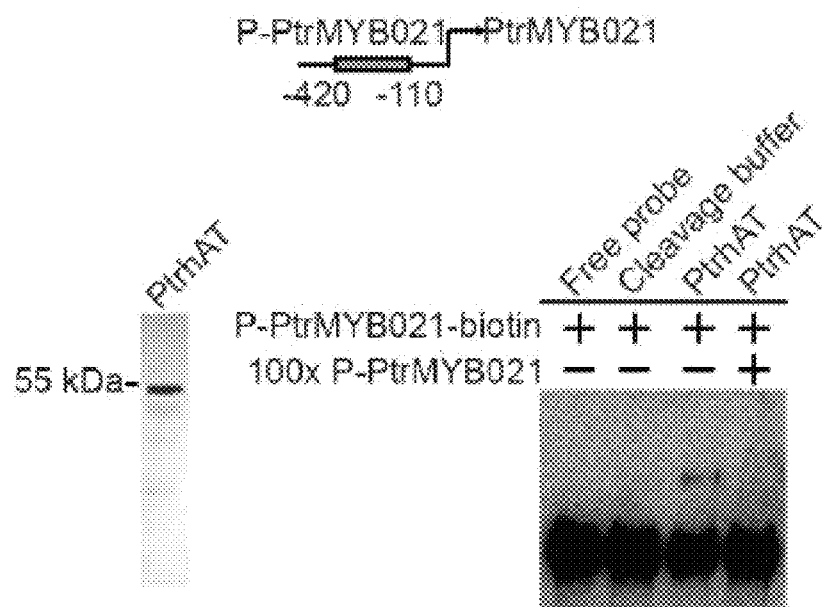
Figure 4E:
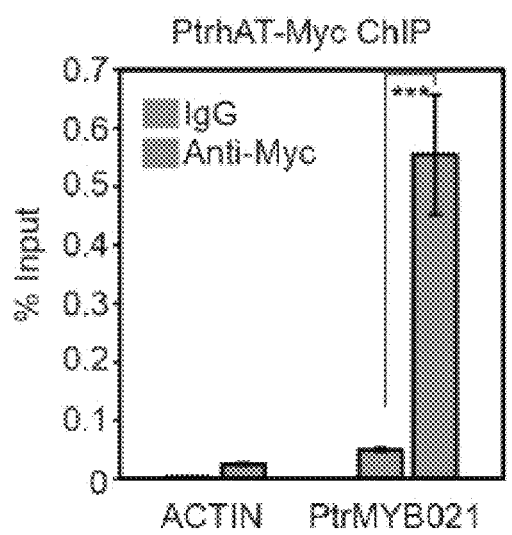
Figures 4F, 4G:
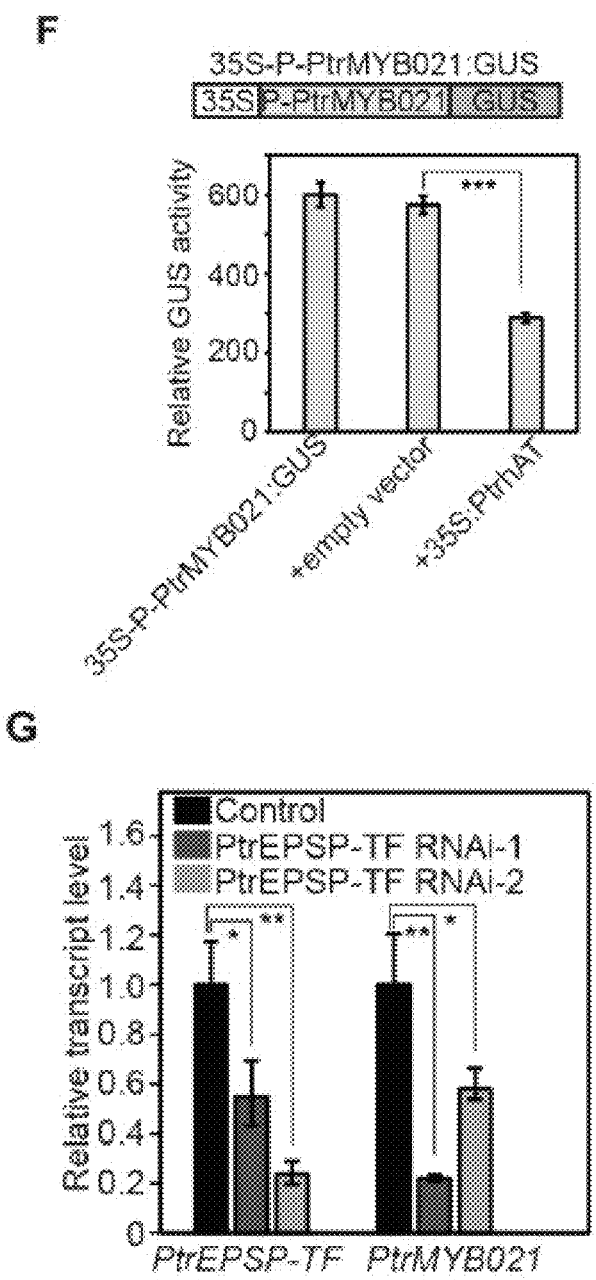

Example 9: PtrhAT Directly Binds to the PtrMYB021 Promoter and Represses PtrMYB021 Expression Results showing that both PtrEPSP-TF and its direct target PtrhAT are repressors prompted us to examine whether PtrhAT directly targets Potri.009G053900 (PtrMYB021) and/or Potri.011G153300 (NST1), which are up-regulated in PtrEPSP-TF overexpression lines. If this is the case, by suppressing PtrhAT expression, PtrEPSP-TF would up-regulate the expression of master regulators of secondary cell wall biosynthesis, which would be consistent with the RNA-seq results. To test this possibility, the inventors expressed and purified PtrhAT in vitro (FIG. 4D) and used it for in vitro EMSA. As expected, PtrhAT specifically bound to a 310-bp PtrMYB021 promoter (−420 to −110 nt from the start codon; FIG. 4D). However, no binding to the NST1 promoter was detected. Consistent with the EMSA results, the µChIP results also showed drastic enrichment of the PtrMYB021 promoter in PtrhAT precipitates (FIG. 4E), illustrating in vivo binding of PtrhAT to the PtrMYB021 promoter. By inserting the PtrMYB021 promoter (−420 to −110 nt from the start codon) between 35S promoter and the GUS reporter gene (35S-PPtrMYB021:GUS) in the reporter construct for repressor activity analysis, the inventors examined the effect of PtrhAT on PtrMYB021 promoter activity. As predicted, PtrhAT reduced the activity of the PtrMYB021 promoter (FIG. 4F).

Systematically, the inventors conclude that PtrMYB021 is a direct target of PtrhAT. Combined with the functional characterization of PtrEPSP-TF, the inventors have found that PtrEPSP-TF and PtrhAT form a previously undescribed hierarchical transcriptional regulation on PtrMYB021 expression. In support of this model, the knockdown of PtrEPSP-TF via RNAi reduced the transcript level of PtrMYB021 in *Populus* (FIG. 4G).

Example 10: Transcriptional Regulation of PtrEPSP-TF by PtWND1B

Figure 5A:
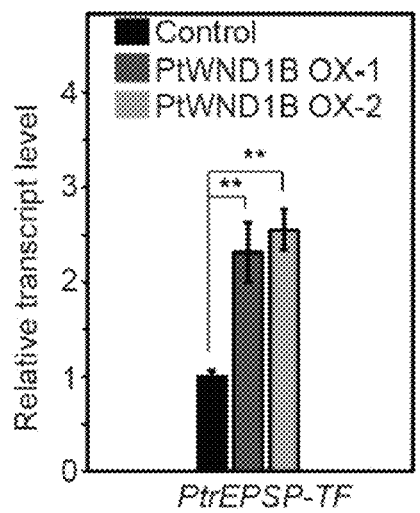
FIGS. 5A-5B. PtrEPSP-TF/PtrhAT mechanism is a novel transcription regulatory hierarchy regulating MYB46 expression and the phenylpropanoid pathway in *Populus*. (A) Transcriptional response of PtrEPSP-TF to overexpression of PtWND1B, the homolog of *Arabidopsis* SND1. RT-qPCR analysis was performed in triplicate to calculate the mean value and standard deviation (error bar), which were used in Student's t-tests. P value comparison was calculated using two-tailed Student's t-tests (** P<0.01, * P<0.05, ns P>0.05). (B) A simplified scheme illustrating the transcriptional regulation of the PtrEPSP-TF/PtrhAT mechanism in MYB46 expression and the phenylpropanoid pathway. Solid line indicates processes studied in this work. The dashed line indicates processes unstudied in this work. Green color indicates transcriptional activation. Red color indicates transcriptional repression.
Figure 5B:
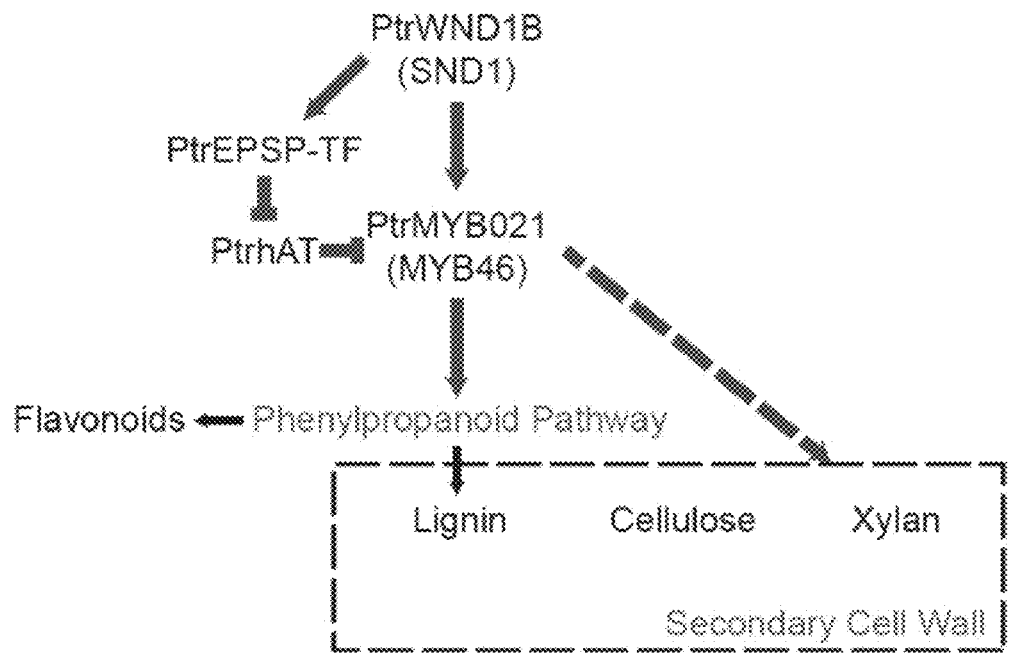

Current *Arabidopsis* and *Populus* models of the transcriptional regulatory hierarchy of secondary cell wall biosynthesis is that SND1 (PtWNDs in *Populus*) activates MYB46 (PtMYB002, PtMYB003, PtMYB020, and PtrMYB021 in *Populus*) and the expression of downstream genes (Kim et al., 2014; Kim et al., 2013b; McCarthy et al., 2010; Zhong et al., 2013; Zhong et al., 2007; Zhong and Ye, 2010). To place the PtrEPSPTF/PtrhAT mechanism into the current model, the inventors evaluated whether PtrEPSP-TF is downstream of SND1 in the transcriptional regulation of MYB46 in *Populus*. RT-qPCR analysis showed that PtrEPSP-TF was up-regulated in two independent *Populus* transgenic lines overexpressing PtWND1B (homolog of SND1 (Ohtani et al., 2011; Zhao et al., 2014)) relative to the empty vector control (FIG. 5A), suggesting that the PtrEPSP-TF/PtrhAT mechanism is downstream of SND1.

Example 11: The HTH Motif is Highly Variable in the Plant Kingdom

Finally, since the HTH motif is not found in homologs of the ancestral prokaryotic progenitor of EPSP synthase, penetrance of this motif was assessed in plants by surveying 57 EPSP synthase isoforms derived from 42 phylogenetically distributed plant genomes. As previously observed (Garg et al., 2014 and Tohge et al., 2013), phylogenetic relatedness of sequences reflects the broader classification delineating monocot, dicot, non-vascular and algal clades of the kingdom plantae. The most striking observation was that the HTH motif was almost entirely missing in non-vascular, algal and monocots clades, but interestingly was found in many dicots. Sequence alignments suggested that, unlike other plants, dicots share a start codon and a conserved MAQV(A/L/I)S(T) (SEQ ID NO: 25) amino acid residue in this additional exon. Functional studies of these sequences are outside the scope of this work and will be required to establish penetrance of the transcriptional regulatory function in other plant species.

Example 12

Figures 7A, 7B:
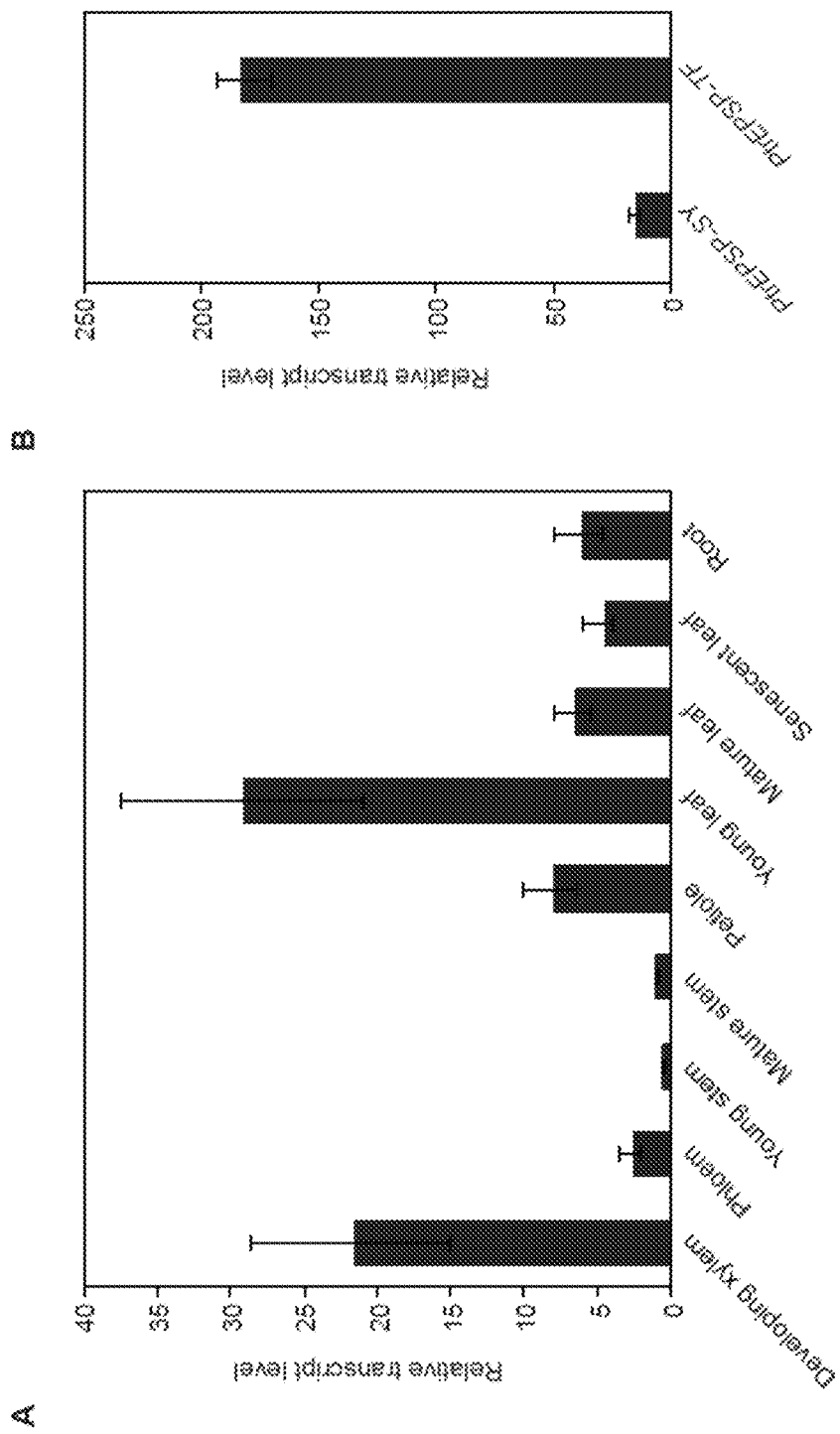
FIGS. 7A-7B. PtrEPSP-TF, but not PtrEPSP-SY, exhibits high expression level in developing xylem tissue. (A) Transcript levels of PtrEPSP-TF in various tissues. Transcript levels are normalized using the expression of housekeeping genes (18S ribosomal RNA and Ubiquitin-conjugating enzyme E2). (B) Transcript levels of PtrEPSP-TF and PtrEPSP-SY in developing xylem. Transcript levels are normalized using the expression of housekeeping genes (18S ribosomal RNA and Ubiquitin-conjugating enzyme E2). The transcript level of PtrEPSP-SY is set as 1. RT-qPCR analysis of transcript levels in this figure was performed in triplicate to calculate the mean value and standard deviation (error bar).

For decades, EPSP synthases were believed to have the single function of catalyzing the conversion from shikimate-3-phosphate to 5-enolpyruvylshikimate-3-phosphate in the shikimate pathway in prokaryotes and eukaryotes (Maeda and Dudareva, 2012; Mir et al., 2015). In plants, the shikimate pathway is upstream of the phenylpropanoid pathway and provides phenylalanine for the biosynthesis of phenylpropanoid compounds (Tohge et al., 2013). The present disclosure provides evidence for an unrelated function of a *Populus* isoform, PtrEPSP-TF, that indirectly regulates the expression of MYB46, a master regulator of the phenylpropanoid pathway and secondary cell wall biosynthesis. Although PtrEPSP-TF retains EPSP synthase activity, its enzymatic activity is much weaker than PtrEPSP-SY (FIG. 2B). With an additional N-terminal HTH DNA-binding motif, PtrEPSP-TF exhibited nuclear accumulation and functioned as a transcriptional repressor (FIGS. 2 and 3B). The subcellular localization and cell fraction results demonstrated that PtrEPSP-TF protein, but not its paralog PtrEPSP-SY, accumulates in the nucleus (FIGS. 2D and E). The abundance of PtrEPSP-TF, but not PtrEPSP-SY or any other enzymes involved in the shikimate pathway, was found to increase during primary to secondary growth of *Populus* stem development (Liu et al., 2015). To support this observation, the inventors found that the expression of PtrEPSP-TF was highest in the relatively chloroplast-devoid developing xylem tissue, where PtrEPSP-SY exhibited extremely low expression in the same tissue (FIGS. 7A-7B). These findings were reinforced by an independent proteomic study on nuclear-enriched proteins from *Populus* developing xylem (Loziuk et al., 2015). In that study, peptides aligning to the N-terminus of PtrEPSP-TF, but not PtrEPSP-SY, were detected, again suggesting a nuclear presence for the PtrEPSP-TF protein. Although the direct mechanism underlying the observed nuclear presence remains to be determined, a possible explanation is that other proteins interact with PtrEPSP-TF and block the effect of the N-terminal chloroplast transit peptide, mimicking the effect observed after the N-terminus was tagged leading to almost 100% nuclear localization. The ChIP and EMSA results demonstrated that unlike PtrEPSP-SY, PtrEPSP-TF does have DNA binding activity and directly binds to its target (i.e., PtrhAT promoter) under both in vivo and in vitro conditions (FIG. 3). Physiologically, the level of lignin biosynthesis during secondary growth is higher than that during primary growth, which requires more monolignols produced via the phenylpropanoid pathway. Considering PtrEPSP-TF is capable of activating the expression of MYB46 and subsequently activating the phenylpropanoid pathway, the accumulation of PtrEPSP-TF proteins from primary to secondary growth in developing xylem is consistent with the regulatory function that the inventors described.

Being one close homolog of *Arabidopsis* MYB46, *Populus* PtrMYB021 regulates not only the phenylpropanoid pathway and lignin biosynthesis, but also the biosynthesis of cellulose and xylan (Zhong et al., 2013). As an upstream regulator of PtrMYB021, PtrEPSP-TF also displayed tight association with lignin biosynthesis and the phenylpropanoid pathway in *Populus*. In addition to lignin biosynthesis, multiple genes involved in xylan and cellulose biosynthesis were up-regulated in PtrEPSP-TF overexpression *Populus*. Whether PtrMYB021 has similar effects as PtrMYB021 on the biosynthesis of xylan and cellulose merits future research. Among the two master regulators with increased expression levels in PtrEPSP-TF overexpression *Populus* plants, the roles of PtrMYB021 in secondary cell wall formation have been well established. However, the functions of Potri.011G153300 (NST1) remain poorly studied in *Populus*.

The phenylpropanoid pathway provides key secondary metabolites for secondary cell wall formation and plant immunity. As such, the regulation of MYB46 expression is critical for plants to respond to various developmental and environmental changes. Currently, only the mechanism that SND1 directly activates, MYB46 expression, has been well studied in both *Arabidopsis* and *Populus* (Ohtani et al., 2011; Zhong et al., 2007). Such a singular regulatory mechanism seems vulnerable and insufficient to comprehensively regulate MYB46 expression and the phenylpropanoid pathway under diverse and variable developmental and environmental changes experienced by long-lived perennials. The PtrEPSP-TF/PtrhAT mechanism identified in this disclosure broadens the understanding of the regulation of MYB46 expression, and concomitantly the phenylpropanoid pathway, and provides additional targets for engineering the phenylpropanoid pathway to meet the needs of the bioeconomy. Further, the role of SLEEPER hAT transposase family genes in regulating gene expression is poorly studied. This disclosure illustrates the involvement of a SLEEPER gene in the transcriptional regulation of the phenylpropanoid pathway.

It is intriguing that this shikimate pathway derived-EPSP synthase isoform appears to have obtained a regulatory function modulating expression of processes that are ubiquitous in dicots relative to other plants. With this in mind, the inventors have hypothesized that domain co-option may have occurred during the course of evolution when early dicotyledonous plants attained complex cell wall structure (Tohge et al., 2013; Weng et al., 2008).

Finally, the present characterization of the molecular mechanism linking PtrEPSP-TF function to lignin and subsequently phenylpropanoid biosynthesis in *Populus* provides a solid foundation for functional studies and confirmation of discoveries from association mapping studies. As it is becoming rapidly clear that model system-based studies have significant limitations in informing the biology of complex organisms, data-driven, non-inference-based methods of linking genes to phenotypes hold tremendous potential in facilitating discovery in target plant species.

What is claimed is:

1. A genetically modified plant, plant cell or plant tissue of the *Populus* genus, the genetic modification comprising overexpressing a PtrhAT gene, in the plant, plant cell or plant tissue, wherein the PtrhAT gene encodes a protein comprising the amino acid sequence of SEQ ID NO 2.

2. The genetically modified plant, plant cell or plant tissue of claim 1, wherein the PtrhAT gene comprises the nucleotide sequence of SEQ ID NO: 1.

3. A method comprising genetically modifying a plant, plant cell or plant tissue of the *Populus* genus plant, wherein the genetic modifying comprises overexpressing a PtrhAT gene in the plant, plant cell or plant tissue, wherein the PtrhAT gene encodes a protein comprising the amino acid sequence of SEQ ID NO: 2.

4. The method of claim 3, wherein the PtrhAT gene comprises the nucleotide sequence of SEQ ID NO: 1.

5. A method for producing a bioproduct, comprising subjecting the genetically modified plant, plant cell or plant tissue of claim 1 to a bioproduct conversion process.

6. The method of claim 5, wherein the bioproduct is selected from the group consisting of a bioenergy product, a biomaterial, a biopharmaceutical and a biocosmetics.

7. The method of claim 6, wherein the bioenergy product is ethanol and the bioproduct conversion process is an ethanol fermentation process.

8. The method of claim 6, wherein the bioproduct is selected from the group consisting of ethanol, biodiesel, biogas, bioplastics, biofoams, biorubber, biocomposites, and biofibres.

9. A method for production of pulp or paper, comprising producing pulp or paper from the genetically modified plant of claim 1.

* * * * *

SEQUENCE LISTING

<160> NUMBER OF SEQ ID NOS: 25

<210> SEQ ID NO 1
<211> LENGTH: 1335
<212> TYPE: DNA
<213> ORGANISM: Populus balsamifera subsp. trichocarpa

<400> SEQUENCE: 1

```
atggggactg tacatgaagt ctttaaaagt gtgcttgcag agtggagcat caacaagaac      60
```

```
gttcgcttca tattcctgga tataactcct ccaaacgatc acatgattgg agaattaaga      120
agtaaggttt ctgatcaagc cccacctatc catggacatc ttttctgtgt tcctagttat      180
gcccacattc tcagtctcct tgttcaagat ggattttctg agataaggag tgtgctttat      240
aagataagag aatgtataga gtacgtcaaa ggaagctcac ttgtaaggca gaggttccag      300
gaggcaatta ataatgggag tttgcaggac agggaaatgc ctactctaga tgttgccgcg      360
agatgggaca ccacctttct tatgctggag agttcattgg aatttagaac agcttttaat      420
caccttgagc aattggatga tgatttcaaa gtgaatccat ctgcagaaga atggaacaaa      480
gcaacagccg tatttgagtg cttgaaagag ttctacaatt caacatgcaa ttttccaaca      540
agcagagatg attatttcct cagtgttcgt gatgtttata agaacttgca aggctggaaa      600
cagagcgatt atgtatatgt tcgcgctatg gcaaatagaa tgaagggaaa atttgacgag      660
tattggggag aagctagctt ggctttggga atctcagcag ttcttgaccc cagctttaaa      720
ttggacatta ttgagtatgg ctaccggcag atatacggca gtgatgctga cttgcactta      780
tccagattcc gttacgatct tacatgtgca taccataaat atgcaaagga catcagcaat      840
cagggaccat cttcttctgc catggctgaa gtgggtcgtt gtacatcatc tgatattagt      900
ttcaaagagt ggcgcaaggg taagtatgaa cgcaacatgg tgccctcaca atggaatgag      960
cttgatcagt atctacaact gcccccggag aacttggata aggatggtaa cgtattagct     1020
tggtggcaag acaatgctcc aaattttcca atactgggaa aaatggctcg tgatttctta     1080
gcaattccag tatcaactgt catttccaag tcatcagagg ttatgaagat ggcatcagtc     1140
catgacggtg ttcgtcctga gatagccgag gctttgatat gtggaaagga ttggttggac     1200
agccctaact gcaagttttc cttttctttt tgatctatt taagtgtgat gcgtttatat      1260
ctctgctatc tgtttatta tttcttcttc ttcttttctt cagcaattga tccatgtttg      1320
gatcctcact ggtag                                                      1335

<210> SEQ ID NO 2
<211> LENGTH: 444
<212> TYPE: PRT
<213> ORGANISM: Populus balsamifera subsp. trichocarpa

<400> SEQUENCE: 2

Met Gly Thr Val His Glu Val Phe Lys Ser Val Leu Ala Glu Trp Ser
 1               5                  10                  15

Ile Asn Lys Asn Val Arg Phe Ile Phe Leu Asp Ile Thr Pro Pro Asn
            20                  25                  30

Asp His Met Ile Gly Glu Leu Arg Ser Lys Val Ser Asp Gln Ala Pro
        35                  40                  45

Pro Ile His Gly His Leu Phe Cys Val Pro Ser Tyr Ala His Ile Leu
    50                  55                  60

Ser Leu Leu Val Gln Asp Gly Phe Ser Glu Ile Arg Ser Val Leu Tyr
65                  70                  75                  80

Lys Ile Arg Glu Cys Ile Glu Tyr Val Lys Gly Ser Ser Leu Val Arg
                85                  90                  95

Gln Arg Phe Gln Glu Ala Ile Asn Asn Gly Ser Leu Gln Asp Arg Glu
            100                 105                 110

Met Pro Thr Leu Asp Val Ala Ala Arg Trp Asp Thr Thr Phe Leu Met
        115                 120                 125

Leu Glu Ser Ser Leu Glu Phe Arg Thr Ala Phe Asn His Leu Glu Gln
    130                 135                 140
```

```
Leu Asp Asp Asp Phe Lys Val Asn Pro Ser Ala Glu Glu Trp Asn Lys
145                 150                 155                 160

Ala Thr Ala Val Phe Glu Cys Leu Lys Glu Phe Tyr Asn Ser Thr Cys
                165                 170                 175

Asn Phe Pro Thr Ser Arg Asp Asp Tyr Phe Leu Ser Val Arg Asp Val
            180                 185                 190

Tyr Lys Asn Leu Gln Gly Trp Lys Gln Ser Asp Tyr Val Tyr Val Arg
        195                 200                 205

Ala Met Ala Asn Arg Met Lys Gly Lys Phe Asp Glu Tyr Trp Gly Glu
    210                 215                 220

Ala Ser Leu Ala Leu Gly Ile Ser Ala Val Leu Asp Pro Ser Phe Lys
225                 230                 235                 240

Leu Asp Ile Ile Glu Tyr Gly Tyr Arg Gln Ile Tyr Gly Ser Asp Ala
                245                 250                 255

Asp Leu His Leu Ser Arg Phe Arg Tyr Asp Leu Thr Cys Ala Tyr His
            260                 265                 270

Lys Tyr Ala Lys Asp Ile Ser Asn Gln Gly Pro Ser Ser Ala Met
        275                 280                 285

Ala Glu Val Gly Arg Cys Thr Ser Ser Asp Ile Ser Phe Lys Glu Trp
    290                 295                 300

Arg Lys Gly Lys Tyr Glu Arg Asn Met Val Pro Ser Gln Trp Asn Glu
305                 310                 315                 320

Leu Asp Gln Tyr Leu Gln Leu Pro Pro Glu Asn Leu Asp Lys Asp Gly
                325                 330                 335

Asn Val Leu Ala Trp Trp Gln Asp Asn Ala Pro Asn Phe Pro Ile Leu
            340                 345                 350

Gly Lys Met Ala Arg Asp Phe Leu Ala Ile Pro Val Ser Thr Val Ile
        355                 360                 365

Ser Lys Ser Ser Glu Val Met Lys Met Ala Ser Val His Asp Gly Val
370                 375                 380

Arg Pro Glu Ile Ala Glu Ala Leu Ile Cys Gly Lys Asp Trp Leu Asp
385                 390                 395                 400

Ser Pro Asn Cys Lys Phe Ser Phe Phe Phe Leu Ile Tyr Leu Ser Val
                405                 410                 415

Met Arg Leu Tyr Leu Cys Tyr Leu Phe Ile Tyr Phe Phe Phe Phe Phe
            420                 425                 430

Ser Ser Ala Ile Asp Pro Cys Leu Asp Pro His Trp
        435                 440

<210> SEQ ID NO 3
<211> LENGTH: 1557
<212> TYPE: DNA
<213> ORGANISM: Populus balsamifera subsp. trichocarpa

<400> SEQUENCE: 3
atggctcaag tgagcaaaat cagcaatgga gcacaaaaca cctacacaac aatccatctt     60
ttaaaacccc aaatacccaa atctttgtct tcaatttcat ttagatcaca gctcattaaa    120
gggtcttctt ttggttttgaa gcaatgtaaa aaaatgggta gttgcaagct aaaggttgaa    180
cctttgaagg ttttagcttc aattgctaca gcagagaagc catcaactgt acctgagatc    240
gttttgcaac ccatcaaaga tatttctggt actgttactt taccgggttc caagtctctg    300
tcaaatcgga tactccttct tgctgctctc tctgagggta cgactgttgt tgacaatttg    360
ttgaatagtg atgatgttca ttacatgctt ggcgcgctaa gaacacttgg cctacatgtg    420
```

```
gaagataata agaaactcaa acaagcaatt gtagaaggat gtggtggcca gtttcctgtg    480
ggaaaagaag caaatgttga tgttgaactt ttccttggaa atgctggaac agcaatgcgt    540
ccattgacag ctgctgtaac tgctgcaggt ggaaattcaa gctatatact tgatggggtg    600
ccacgaatga gggagagacc aattggtgat ttggttattg gtcttcagca gcttggtgca    660
gatgtttctt gttctcctac aaactgcccc cctgttcgca taaatgcaaa tgggggcctt    720
ccagggggaa aggttaaact ctctggatct ataagtagtc aatacttgac tgctttgctc    780
atggcagctc ctttagctct tggagatgtg gaaattgaga tcgttgacaa attgatttct    840
gttccatatg ttgagatgac tctgaagttg atggagcgct atggagtctt tgtagaacac    900
agtgataact gggatcgttt ctttgttcga ggaggtcaaa agtacaagtc tcctaaaaat    960
tcttttgttg agggcgatgc ttcaagtgcc agttacttcc tagctggtgc agcaatcact   1020
ggtgggacca tcactgtcga aggttgtggg atggatagtt tgcagggaga gtaaagtttt   1080
gcagaggttc ttgagaaaat gggagccaaa gttacttgga caagaacag tgttactgtc    1140 actggaccgc cacgagattc ttctggtcag aaacacttgc gtgctgtcga tgtaaacatg   1200
aacaaaatgc cagatgttgc tatgactctg gctgttgttg cgcttttcgc tgatggtcct   1260
actgccataa gagatgtggc aagttggaga gtgaaagaaa cagaacggat gattgctatt   1320
tgcacagaac taaggaagtt gggagcaaca gttgaagaag gaccagatta ctgtgtgatc   1380
actccacctg agaaactaaa tgtgacagag attgacactt atgatgatca caggatggca   1440
atggcattct ctcttgctgc ttgtggagaa gtccaagtca ccatcaagga ccctggttgc   1500
actcgaaaaa ctttcccaga ctactttgag gttcttgaga ggtacacaaa gcattga       1557

<210> SEQ ID NO 4
<211> LENGTH: 518
<212> TYPE: PRT
<213> ORGANISM: Populus balsamifera subsp. trichocarpa

<400> SEQUENCE: 4

Met Ala Gln Val Ser Lys Ile Ser Asn Gly Ala Gln Asn Thr Tyr Thr
1               5                   10                  15

Thr Ile His Leu Leu Lys Pro Gln Ile Pro Lys Ser Leu Ser Ser Ile
            20                  25                  30

Ser Phe Arg Ser Gln Leu Ile Lys Gly Ser Ser Phe Gly Leu Lys Gln
        35                  40                  45

Cys Lys Lys Met Gly Ser Cys Lys Leu Lys Val Glu Pro Leu Lys Val
    50                  55                  60

Leu Ala Ser Ile Ala Thr Ala Glu Lys Pro Ser Thr Val Pro Glu Ile
65                  70                  75                  80

Val Leu Gln Pro Ile Lys Asp Ile Ser Gly Thr Val Thr Leu Pro Gly
                85                  90                  95

Ser Lys Ser Leu Ser Asn Arg Ile Leu Leu Leu Ala Ala Leu Ser Glu
            100                 105                 110

Gly Thr Thr Val Val Asp Asn Leu Leu Asn Ser Asp Asp Val His Tyr
        115                 120                 125

Met Leu Gly Ala Leu Arg Thr Leu Gly Leu His Val Glu Asp Asn Lys
    130                 135                 140

Lys Leu Lys Gln Ala Ile Val Glu Gly Cys Gly Gly Gln Phe Pro Val
145                 150                 155                 160

Gly Lys Glu Ala Asn Val Asp Val Glu Leu Phe Leu Gly Asn Ala Gly
                165                 170                 175
```

```
Thr Ala Met Arg Pro Leu Thr Ala Ala Val Thr Ala Ala Gly Gly Asn
            180                 185                 190
Ser Ser Tyr Ile Leu Asp Gly Val Pro Arg Met Arg Glu Arg Pro Ile
        195                 200                 205
Gly Asp Leu Val Ile Gly Leu Gln Gln Leu Gly Ala Asp Val Ser Cys
    210                 215                 220
Ser Pro Thr Asn Cys Pro Pro Val Arg Ile Asn Ala Asn Gly Gly Leu
225                 230                 235                 240
Pro Gly Gly Lys Val Lys Leu Ser Gly Ser Ile Ser Ser Gln Tyr Leu
                245                 250                 255
Thr Ala Leu Leu Met Ala Ala Pro Leu Ala Leu Gly Asp Val Glu Ile
            260                 265                 270
Glu Ile Val Asp Lys Leu Ile Ser Val Pro Tyr Val Glu Met Thr Leu
        275                 280                 285
Lys Leu Met Glu Arg Tyr Gly Val Phe Val Glu His Ser Asp Asn Trp
    290                 295                 300
Asp Arg Phe Phe Val Arg Gly Gly Gln Lys Tyr Lys Ser Pro Lys Asn
305                 310                 315                 320
Ser Phe Val Glu Gly Asp Ala Ser Ser Ala Ser Tyr Phe Leu Ala Gly
                325                 330                 335
Ala Ala Ile Thr Gly Gly Thr Ile Thr Val Glu Gly Cys Gly Met Asp
            340                 345                 350
Ser Leu Gln Gly Asp Val Lys Phe Ala Glu Val Leu Glu Lys Met Gly
        355                 360                 365
Ala Lys Val Thr Trp Thr Lys Asn Ser Val Thr Val Thr Gly Pro Pro
    370                 375                 380
Arg Asp Ser Ser Gly Gln Lys His Leu Arg Ala Val Asp Val Asn Met
385                 390                 395                 400
Asn Lys Met Pro Asp Val Ala Met Thr Leu Ala Val Val Ala Leu Phe
                405                 410                 415
Ala Asp Gly Pro Thr Ala Ile Arg Asp Val Ala Ser Trp Arg Val Lys
            420                 425                 430
Glu Thr Glu Arg Met Ile Ala Ile Cys Thr Glu Leu Arg Lys Leu Gly
        435                 440                 445
Ala Thr Val Glu Glu Gly Pro Asp Tyr Cys Val Ile Thr Pro Pro Glu
    450                 455                 460
Lys Leu Asn Val Thr Glu Ile Asp Thr Tyr Asp Asp His Arg Met Ala
465                 470                 475                 480
Met Ala Phe Ser Leu Ala Ala Cys Gly Glu Val Gln Val Thr Ile Lys
                485                 490                 495
Asp Pro Gly Cys Thr Arg Lys Thr Phe Pro Asp Tyr Phe Glu Val Leu
            500                 505                 510
Glu Arg Tyr Thr Lys His
        515
```

<210> SEQ ID NO 5
<211> LENGTH: 1173
<212> TYPE: DNA
<213> ORGANISM: Populus balsamifera subsp. trichocarpa

<400> SEQUENCE: 5

```
atgcttggtg cactcagaac acttggacta tgtttggaag agaacacgga actcgaacaa      60
gtgatcgtag aaggttgtgg tggtcagttt ccagtgggaa agaagcaaa gattgatgtt     120
ggacttttcc ttggaaatgc tggaacggca atgcggccat ttacagctgc agttactgct     180
```

-continued

```
gcaggtggaa atttgagcta catacttgat ggggtgtcac gaatgagaga gagaccaatt       240
ggtgatttgg ttattggtct tcagcagctt ggtgcagatg tttcttgttc tcctacaaac       300
tgcccccctg ttcgtgtaaa tgcaaatgga ggccttccag ggggaaaggt taaactcgct       360
ggatcgataa gtagtcaata cttgactgct ttgctcatgg cagctccttt agcccttgga       420
gatgtggaaa ttgagataat agacaagttg atttctgttc cttatgttga gatgacttta       480
aagttgatgg agcgctatgg agtctttata caacatagtg atagctggga tcgtttcttc       540
attcgaggag gtcaaaaata caagtctcct ggaaattctt ttgttgaggg tgatgcttca       600
agtgccggtt acttcctagc tggcgcagca atcactggtg gaccatcac tgttgaaggt        660 tgtggaacag acagtttgca gggagatgta aaatttgcag aggttcttga gaaatggga        720 gctaaagtta cctggaccaa gaacagtgtt actgtcactg gactgccacg agattcttct       780
ggttggaaac acttgcgtgc tgttgatgta acatgaaca aaatgccaga tgttgctatg        840
actctggctg ttgttgcgct tttcaccaat ggccctactg ccataagaga tgtggcaagt       900
tggagagtga agaaatgga acggatgatt gctatttgga aggaactcag gaagttggga       960
gcaacagttg aagaaggacc agattactgt gtgattaccc cccctgagaa actaaatgta      1020
acagagattg acacttacga tgatcacagg atggcaatgg cattctctct tgctgcttgg      1080
ggagaagtcc cagtcaccat caaggacccg ggtggcactg gaaaaacttt cccagactac      1140
tttgaagtcc ttgaggggta cacgaagcat tga                                   1173
```

<210> SEQ ID NO 6
<211> LENGTH: 390
<212> TYPE: PRT
<213> ORGANISM: Populus balsamifera subsp. trichocarpa

<400> SEQUENCE: 6

```
Met Leu Gly Ala Leu Arg Thr Leu Gly Leu Cys Leu Glu Glu Asn Thr
1               5                   10                  15

Glu Leu Glu Gln Val Ile Val Glu Gly Cys Gly Gly Gln Phe Pro Val
            20                  25                  30

Gly Lys Glu Ala Lys Ile Asp Val Gly Leu Phe Leu Gly Asn Ala Gly
        35                  40                  45

Thr Ala Met Arg Pro Phe Thr Ala Ala Val Thr Ala Ala Gly Gly Asn
    50                  55                  60

Leu Ser Tyr Ile Leu Asp Gly Val Ser Arg Met Arg Glu Arg Pro Ile
65                  70                  75                  80

Gly Asp Leu Val Ile Gly Leu Gln Gln Leu Gly Ala Asp Val Ser Cys
                85                  90                  95

Ser Pro Thr Asn Cys Pro Pro Val Arg Val Asn Ala Asn Gly Gly Leu
            100                 105                 110

Pro Gly Gly Lys Val Lys Leu Ala Gly Ser Ile Ser Ser Gln Tyr Leu
        115                 120                 125

Thr Ala Leu Leu Met Ala Ala Pro Leu Ala Leu Gly Asp Val Glu Ile
    130                 135                 140

Glu Ile Ile Asp Lys Leu Ile Ser Val Pro Tyr Val Glu Met Thr Leu
145                 150                 155                 160

Lys Leu Met Glu Arg Tyr Gly Val Phe Ile Gln His Ser Asp Ser Trp
                165                 170                 175

Asp Arg Phe Phe Ile Arg Gly Gly Gln Lys Tyr Lys Ser Pro Gly Asn
            180                 185                 190
```

```
Ser Phe Val Glu Gly Asp Ala Ser Ala Gly Tyr Phe Leu Ala Gly
        195                 200                 205

Ala Ala Ile Thr Gly Gly Thr Ile Thr Val Glu Gly Cys Gly Thr Asp
210                 215                 220

Ser Leu Gln Gly Asp Val Lys Phe Ala Glu Val Leu Glu Lys Met Gly
225                 230                 235                 240

Ala Lys Val Thr Trp Thr Lys Asn Ser Val Thr Val Thr Gly Leu Pro
                245                 250                 255

Arg Asp Ser Ser Gly Trp Lys His Leu Arg Ala Val Asp Val Asn Met
            260                 265                 270

Asn Lys Met Pro Asp Val Ala Met Thr Leu Ala Val Val Ala Leu Phe
        275                 280                 285

Thr Asn Gly Pro Thr Ala Ile Arg Asp Val Ala Ser Trp Arg Val Lys
    290                 295                 300

Glu Met Glu Arg Met Ile Ala Ile Trp Lys Glu Leu Arg Lys Leu Gly
305                 310                 315                 320

Ala Thr Val Glu Glu Gly Pro Asp Tyr Cys Val Ile Thr Pro Pro Glu
                325                 330                 335

Lys Leu Asn Val Thr Glu Ile Asp Thr Tyr Asp Asp His Arg Met Ala
            340                 345                 350

Met Ala Phe Ser Leu Ala Ala Trp Gly Glu Val Pro Val Thr Ile Lys
        355                 360                 365

Asp Pro Gly Gly Thr Gly Lys Thr Phe Pro Asp Tyr Phe Glu Val Leu
    370                 375                 380

Glu Gly Tyr Thr Lys His
385                 390

<210> SEQ ID NO 7
<211> LENGTH: 999
<212> TYPE: DNA
<213> ORGANISM: Populus balsamifera subsp. trichocarpa

<400> SEQUENCE: 7
atgaggaagc cagaggcctc tgggaagaac aacgttaata acattaacaa gttcagaaag      60
ggcttgtggt caccagagga agatgacaag ctcatgaact acatgctaaa caatggacaa     120
ggttgctgga gtgatgtggc aaggaatgct ggtttgcagc gatgcggcaa gagttgccgg     180
cttcgttgga ttaattactt gaggcctgat ctcaagagag tgcattttc  accccaagaa     240 gaagagatga tcatccattt gcattccctt ctcggcaata ggtggtctca aattgcggct     300
cgcttgccag gaagaacgga caatgaaatc aagaattttt ggaattcaac aataaagaag     360
agattaaaga tctgcagtc  atccaacgca tcaccaaaca caagtgattc ctcctcggag     420
cctagcaaag atgtcatggg agggttgatg tcgaccatgc aagaacaagg catttctcc      480 atgaacatgg atccttcaat gtcatcttcg tcatcgttag caacctccat gaaagcaatg     540
attctaaata ccatgatgga tccattacta cctatgcttg attatgatca tggcctaaac     600
atgtatggcg gtgcaagtgg gtacgaatcc attaccgcac caccatgcat ggctcaagtt     660
ggagtcctta acgtggtga  tcatggtttt tatggggaag ggatctttga aggtattaat     720
gttgagattc ctcctttaga gagtgtaagc tgcatggagg aaaatgcaaa acccagaat      780 atacaggata caacactga  caagtactca tatagtagtc ctgtgaatag tctttaccac     840
aaaaactgca acatcactag taataacaag acagatagca tagctgctga tcagatgggg     900
aacttatggc acggatcaga agagttaaaa gtgggggagt gggacttgga agagttgatg     960
```
aaagatgttt cggcctttcc attccttgat ttccaatga                999

<210> SEQ ID NO 8
<211> LENGTH: 332
<212> TYPE: PRT
<213> ORGANISM: Populus balsamifera subsp. trichocarpa

<400> SEQUENCE: 8

Met Arg Lys Pro Glu Ala Ser Gly Lys Asn Val Asn Asn Ile Asn
1               5                   10                  15

Lys Phe Arg Lys Gly Leu Trp Ser Pro Glu Glu Asp Asp Lys Leu Met
                20                  25                  30

Asn Tyr Met Leu Asn Asn Gly Gln Gly Cys Trp Ser Asp Val Ala Arg
            35                  40                  45

Asn Ala Gly Leu Gln Arg Cys Gly Lys Ser Cys Arg Leu Arg Trp Ile
        50                  55                  60

Asn Tyr Leu Arg Pro Asp Leu Lys Arg Gly Ala Phe Ser Pro Gln Glu
65                  70                  75                  80

Glu Glu Met Ile Ile His Leu His Ser Leu Leu Gly Asn Arg Trp Ser
                85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Asn Leu Gln Ser Ser
        115                 120                 125

Asn Ala Ser Pro Asn Thr Ser Asp Ser Ser Glu Pro Ser Lys Asp
    130                 135                 140

Val Met Gly Gly Leu Met Ser Thr Met Gln Glu Gln Gly Ile Phe Ser
145                 150                 155                 160

Met Asn Met Asp Pro Ser Met Ser Ser Ser Ser Leu Ala Thr Ser
                165                 170                 175

Met Lys Ala Met Ile Leu Asn Thr Met Met Asp Pro Leu Leu Pro Met
            180                 185                 190

Leu Asp Tyr Asp His Gly Leu Asn Met Tyr Gly Gly Ala Ser Gly Tyr
        195                 200                 205

Glu Ser Ile Thr Ala Pro Pro Cys Met Ala Gln Val Gly Val Leu Asn
    210                 215                 220

Ser Gly Asp His Gly Phe Tyr Gly Glu Gly Ile Phe Glu Gly Ile Asn
225                 230                 235                 240

Val Glu Ile Pro Pro Leu Glu Ser Val Ser Cys Met Glu Glu Asn Ala
                245                 250                 255

Lys Thr Gln Asn Ile Gln Asp Asn Thr Asp Lys Tyr Ser Tyr Ser
            260                 265                 270

Ser Pro Val Asn Ser Leu Tyr His Lys Asn Cys Asn Ile Thr Ser Asn
        275                 280                 285

Asn Lys Thr Asp Ser Ile Ala Ala Asp Gln Met Gly Asn Leu Trp His
    290                 295                 300

Gly Ser Glu Glu Leu Lys Val Gly Glu Trp Asp Leu Glu Glu Leu Met
305                 310                 315                 320

Lys Asp Val Ser Ala Phe Pro Phe Leu Asp Phe Gln
                325                 330

<210> SEQ ID NO 9
<211> LENGTH: 1257
<212> TYPE: DNA
<213> ORGANISM: Populus balsamifera subsp. trichocarpa

<400> SEQUENCE: 9

```
atgcctgagg atatgatgaa tctatcaata aatggtcagt ctcaggtccc tccaggcttt    60
agatttcacc caacagaaga agagcttctt cactactacc tcaggaagaa agttgctaat   120
gagaagatag accttgatgt aattcgcgag gttgatctta ataagcttga gccatgggac   180
atccaagaga agtgcaaaat aggatctaca ccacagaatg attggtattt ctttagtcac   240
aaagacaaga aatatcccac aggactaga acaaatcgag ctacggctgc tgggttttgg   300
aaagccactg gccgtgataa gatcatctat agtgggttta aaagaattgg attgagaaag   360
actcttgtgt tttacagagg aagagctcca catggacaga atccgattg gatcatgcat    420
gaatataggc ttgatgacag caccaacgac actaatgtct caaatcctat aggagaggca   480
atccctgaag aagggtgggt ggtttgccgg gtatttagaa agaagaacta tcaaaaaacc   540
cttgagagtc ccaaaagctc atcatgctca ttggattcaa aggctcatca gattcttggt   600
tcaggaaatg atggagttct tgatcaaata cttctctata tgggaaggac ttgcaagatg   660
gagaatgaaa catttagcaa catgaatatc tccaacaaca acagtagttt aaggtttctc   720
tcagacaata gcatcagtga tgggctccat gaaagattca tgcaccttcc tcggttagac   780
agcccaccac tcccttctat tccactaagc agtccatctt ttgatcaaga tcgaagtttc   840
aaatcttgtt atcaccaatc gtacgatgag atgctgacag agaatgaacc ttcctcttca   900
aaccaaattg gcaatggcac tttcgacatg atctcatcat ccgtaattca tggctccaaa   960
tccgggcaac ttaacgattg ggtaactctt gatcgtctag tggcatcaca acttaatgga  1020
catgaagcag agacatccaa gcatttatct tgctttacta ccggcccaaa tgcgagtttt  1080
ggtctttctc ctgatgatga catgcaatta tcacacttgc aaaattctca tagatcatca  1140
tcaaacattt aagcaaatac ttctcatgtg tataccaacg agaatgacct atggggcttc  1200
actaaatctt cgtctccatc atcatcatcg gacccattat gccacttatc ggtataa     1257
```

<210> SEQ ID NO 10
<211> LENGTH: 418
<212> TYPE: PRT
<213> ORGANISM: Populus balsamifera subsp. trichocarpa

<400> SEQUENCE: 10

```
Met Pro Glu Asp Met Met Asn Leu Ser Ile Asn Gly Gln Ser Gln Val
1               5                   10                  15

Pro Pro Gly Phe Arg Phe His Pro Thr Glu Glu Leu Leu His Tyr
            20                  25                  30

Tyr Leu Arg Lys Lys Val Ala Asn Glu Lys Ile Asp Leu Asp Val Ile
        35                  40                  45

Arg Glu Val Asp Leu Asn Lys Leu Glu Pro Trp Asp Ile Gln Glu Lys
    50                  55                  60

Cys Lys Ile Gly Ser Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Ala
                85                  90                  95

Ala Gly Phe Trp Lys Ala Thr Gly Arg Asp Lys Ile Ile Tyr Ser Gly
            100                 105                 110

Phe Lys Arg Ile Gly Leu Arg Lys Thr Leu Val Phe Tyr Arg Gly Arg
        115                 120                 125

Ala Pro His Gly Gln Lys Ser Asp Trp Ile Met His Glu Tyr Arg Leu
    130                 135                 140
```

-continued

Asp Asp Ser Thr Asn Asp Thr Asn Val Ser Asn Pro Ile Gly Glu Ala
145                 150                 155                 160

Ile Pro Glu Glu Gly Trp Val Val Cys Arg Val Phe Arg Lys Lys Asn
            165                 170                 175

Tyr Gln Lys Thr Leu Glu Ser Pro Lys Ser Ser Cys Ser Leu Asp
        180                 185                 190

Ser Lys Ala His Gln Ile Leu Gly Ser Gly Asn Asp Gly Val Leu Asp
        195                 200                 205

Gln Ile Leu Leu Tyr Met Gly Arg Thr Cys Lys Met Glu Asn Glu Thr
    210                 215                 220

Phe Ser Asn Met Asn Ile Ser Asn Asn Asn Ser Ser Leu Arg Phe Leu
225                 230                 235                 240

Ser Asp Asn Ser Ile Ser Asp Gly Leu His Glu Arg Phe Met His Leu
                245                 250                 255

Pro Arg Leu Asp Ser Pro Pro Leu Pro Ser Ile Pro Leu Ser Ser Pro
            260                 265                 270

Ser Phe Asp Gln Asp Arg Ser Phe Lys Ser Cys Tyr His Gln Ser Tyr
        275                 280                 285

Asp Glu Met Leu Thr Glu Asn Glu Pro Ser Ser Asn Gln Ile Gly
290                 295                 300

Asn Gly Thr Phe Asp Met Ile Ser Ser Ser Val Ile His Gly Ser Lys
305                 310                 315                 320

Ser Gly Gln Leu Asn Asp Trp Val Thr Leu Asp Arg Leu Val Ala Ser
                325                 330                 335

Gln Leu Asn Gly His Glu Ala Glu Thr Ser Lys His Leu Ser Cys Phe
            340                 345                 350

Thr Thr Gly Pro Asn Ala Ser Phe Gly Leu Ser Pro Asp Asp Met
                355                 360                 365

Gln Leu Ser His Leu Gln Asn Ser His Arg Ser Ser Ser Asn Ile Gln
            370                 375                 380

Ala Asn Thr Ser His Val Tyr Thr Asn Glu Asn Asp Leu Trp Gly Phe
385                 390                 395                 400

Thr Lys Ser Ser Ser Pro Ser Ser Ser Ser Asp Pro Leu Cys His Leu
                405                 410                 415

Ser Val

<210> SEQ ID NO 11
<211> LENGTH: 29
<212> TYPE: DNA
<213> ORGANISM: Artificial Sequence
<220> FEATURE:
<223> OTHER INFORMATION: polynucleotide

<400> SEQUENCE: 11 caccccggg aaagccatgg ctcaagtga                                    29

<210> SEQ ID NO 12
<211> LENGTH: 27
<212> TYPE: DNA
<213> ORGANISM: Artificial Sequence
<220> FEATURE:
<223> OTHER INFORMATION: polynucleotide

<400> SEQUENCE: 12
acgcgttttg agtgcaactc aatgctt                                     27

<210> SEQ ID NO 13

```
<211> LENGTH: 30
<212> TYPE: DNA
<213> ORGANISM: Artificial Sequence
<220> FEATURE:
<223> OTHER INFORMATION: polynucleotide

<400> SEQUENCE: 13
caccccgggg gaggttcttg agaggtacac                                         30

<210> SEQ ID NO 14
<211> LENGTH: 27
<212> TYPE: DNA
<213> ORGANISM: Artificial Sequence
<220> FEATURE:
<223> OTHER INFORMATION: polynucleotide

<400> SEQUENCE: 14
tctagattca catatgacca gtctcca                                            27

<210> SEQ ID NO 15
<211> LENGTH: 30
<212> TYPE: DNA
<213> ORGANISM: Artificial Sequence
<220> FEATURE:
<223> OTHER INFORMATION: polynucleotide

<400> SEQUENCE: 15
caccccgggg atgcctgagg atatgatgaa                                         30

<210> SEQ ID NO 16
<211> LENGTH: 28
<212> TYPE: DNA
<213> ORGANISM: Artificial Sequence
<220> FEATURE:
<223> OTHER INFORMATION: polynucleotide

<400> SEQUENCE: 16
acgcgtttgt tataccgata agtggcat                                           28

<210> SEQ ID NO 17
<211> LENGTH: 24
<212> TYPE: DNA
<213> ORGANISM: Artificial Sequence
<220> FEATURE:
<223> OTHER INFORMATION: polynucleotide

<400> SEQUENCE: 17
acctacttcg tttggtcatt gtta                                               24

<210> SEQ ID NO 18
<211> LENGTH: 26
<212> TYPE: DNA
<213> ORGANISM: Artificial Sequence
<220> FEATURE:
<223> OTHER INFORMATION: polynucleotide

<400> SEQUENCE: 18
caaatacaac atactagttc ctccac                                             26

<210> SEQ ID NO 19
<211> LENGTH: 20
<212> TYPE: DNA
<213> ORGANISM: Artificial Sequence
<220> FEATURE:
<223> OTHER INFORMATION: polynucleotide

<400> SEQUENCE: 19
```

```
cccacaacaa tcaacccata                                               20
```

<210> SEQ ID NO 20
<211> LENGTH: 21
<212> TYPE: DNA
<213> ORGANISM: Artificial Sequence
<220> FEATURE:
<223> OTHER INFORMATION: polynucleotide

<400> SEQUENCE: 20

```
ggggaaaata agggaaaaag g                                             21
```

<210> SEQ ID NO 21
<211> LENGTH: 20
<212> TYPE: DNA
<213> ORGANISM: Artificial Sequence
<220> FEATURE:
<223> OTHER INFORMATION: polynucleotide

<400> SEQUENCE: 21

```
tgagcagtaa aacggtttgg                                               20
```

<210> SEQ ID NO 22
<211> LENGTH: 21
<212> TYPE: DNA
<213> ORGANISM: Artificial Sequence
<220> FEATURE:
<223> OTHER INFORMATION: polynucleotide

<400> SEQUENCE: 22

```
ggaaaaggac aagatcatgg a                                             21
```

<210> SEQ ID NO 23
<211> LENGTH: 21
<212> TYPE: DNA
<213> ORGANISM: Artificial Sequence
<220> FEATURE:
<223> OTHER INFORMATION: polynucleotide

<400> SEQUENCE: 23

```
acctgagatc gttttgcaac c                                             21
```

<210> SEQ ID NO 24
<211> LENGTH: 21
<212> TYPE: DNA
<213> ORGANISM: Artificial Sequence
<220> FEATURE:
<223> OTHER INFORMATION: polynucleotide

<400> SEQUENCE: 24

```
caacagtcgt accctcagag a                                             21
```

<210> SEQ ID NO 25
<211> LENGTH: 9
<212> TYPE: PRT
<213> ORGANISM: Artificial Sequence
<220> FEATURE:
<223> OTHER INFORMATION: conserved sequence between dicots

<400> SEQUENCE: 25

```
Met Ala Gln Val Ala Leu Ile Ser Thr
1               5
```